United States Patent
Sasaki et al.

(10) Patent No.: US 7,820,949 B2
(45) Date of Patent: Oct. 26, 2010

(54) METHOD OF STARTING, STOPPING AND OPERATING GAS SENSOR WITH BUILT-IN HEATER

(75) Inventors: Takashi Sasaki, Shioya-gun (JP);
Hiroyuki Abe, Utsunomiya (JP);
Tsuyoshi Eguchi, Utsunomiya (JP);
Akihiro Suzuki, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 140 days.

(21) Appl. No.: 10/514,158

(22) PCT Filed: May 12, 2003

(86) PCT No.: PCT/JP03/05898

§ 371 (c)(1),
(2), (4) Date: Nov. 12, 2004

(87) PCT Pub. No.: WO03/096001

PCT Pub. Date: Nov. 20, 2003

(65) Prior Publication Data

US 2006/0042965 A1    Mar. 2, 2006

(30) Foreign Application Priority Data

May 14, 2002  (JP) .............................. 2002-139094

(51) Int. Cl.
*H05B 1/02* (2006.01)
*H01M 8/00* (2006.01)
*G01N 7/00* (2006.01)

(52) U.S. Cl. ....................... 219/497; 219/494; 219/205; 123/697; 73/23.2; 429/24

(58) Field of Classification Search ................ 219/497, 219/205, 206, 207; 429/12–46; 123/697, 123/703, 220, 672; 73/23.2, 31.01–31.03, 73/31.05, 31.06
See application file for complete search history.

(56) References Cited

U.S. PATENT DOCUMENTS 4,005,001 A    1/1977   Pebler (Continued)

FOREIGN PATENT DOCUMENTS

EP    0466020 A2    1/1992

(Continued)

OTHER PUBLICATIONS

Figaro Engineering Inc., TGS 821—Special Sensor for Hydrogen Gas, Oct. 2004, Figaro Engineering Inc. pp. 1-2.*

(Continued)

*Primary Examiner*—Stephen J Ralis
(74) *Attorney, Agent, or Firm*—Lahive & Cockfield, LLP; Anthony A. Laurentano, Esq.

(57) ABSTRACT

A control apparatus for a gas sensor with a built-in heater is provided which can prevent damage to, deterioration of, and reduction in accuracy of detection of, a gas sensor. When an ignition switch is turned ON, supply of electricity to a heater 27 starts, and when the temperature in the vicinity of a gas sensor 15 (gas temperature of gas detection chamber 24) Ts becomes greater than a predetermined temperature #Ti at start, or when a predetermined electricity supply time after start of supply of electricity to the heater 27 has elapsed, the gas sensor 15 is started. The flow of off-gas is started simultaneously with starting of the gas sensor 15, or after starting. When the ignition switch is turned OFF, the flow of off gas is stopped, and the supply of electric power to the gas sensor 15 is stopped. In a state where a temperature difference ΔT between the gas temperature Ts inside the gas detection chamber 24, and an upstream gas temperature Tg is maintained within a predetermined range, the supply of electricity to the heater 27 is stopped after a predetermined time has elapsed after operation of the gas sensor 15 is stopped.

11 Claims, 10 Drawing Sheets

U.S. PATENT DOCUMENTS

| | | | |
|---|---|---|---|
| 4,063,898 A * | 12/1977 | Fisher | 422/94 |
| 4,298,574 A * | 11/1981 | Bohl | 422/97 |
| 4,531,123 A * | 7/1985 | Tagami et al. | 340/995.28 |
| 4,627,269 A * | 12/1986 | Forster et al. | 73/31.06 |
| 4,753,204 A * | 6/1988 | Kojima et al. | 123/678 |
| 4,765,298 A * | 8/1988 | Kojima et al. | 123/697 |
| 5,898,101 A * | 4/1999 | Lyle et al. | 73/23.2 |
| 6,387,556 B1 * | 5/2002 | Fuglevand et al. | 429/22 |
| 6,668,616 B1 * | 12/2003 | Shoji et al. | 73/23.2 |
| 2001/0045118 A1 * | 11/2001 | Lloyd et al. | 73/1.06 |
| 2002/0081238 A1 * | 6/2002 | Duvinage et al. | 422/168 |
| 2003/0019865 A1 * | 1/2003 | Whitney et al. | 219/497 |
| 2003/0129463 A1 * | 7/2003 | Taguchi et al. | 429/22 |

FOREIGN PATENT DOCUMENTS

| | | |
|---|---|---|
| EP | 0698786 A1 | 2/1996 |
| EP | 1111703 A2 | 6/2001 |
| JP | 2003-294675 | 10/1915 |
| JP | 60-39542 | 3/1985 |
| JP | 60-113141 | 6/1985 |
| JP | 1-182746 | 7/1989 |
| JP | 01182746 A * | 7/1989 |
| JP | 04020834 A * | 1/1992 |
| JP | 4-55751 | 2/1992 |
| JP | 6-223850 | 8/1994 |
| JP | 10-48171 | 2/1998 |
| JP | 2000-221152 | 8/2000 |
| JP | 2001-330578 | 11/2001 |
| JP | 2001-344674 | 12/2001 |

OTHER PUBLICATIONS

European Search Report for Application No. 03728055.9—2204, dated Oct. 26, 2007.

Frank B. Dehn & Co., Explanatory Letter (receipt date stamped).

European Office Action for Application No. 03728055.9-2204, dated Apr. 10, 2008.

* cited by examiner

METHOD OF STARTING, STOPPING AND OPERATING GAS SENSOR WITH BUILT-IN HEATER

RELATED APPLICATIONS

This application is a 35 U.S.C. 371 national stage filing of International Application No. PCT/JP02/05898, filed 12 May 2003, which claims priority to Japanese Patent Application No. 2002-139094 filed on 14 May 2002, in Japan. The contents of the aforementioned applications are hereby incorporated by reference.

TECHNICAL FIELD

The present invention relates to a method of starting, stopping, and operating a gas sensor with a built-in heater, in particular to a method of starting, stopping, and operating, a gas sensor with a built-in heater to prevent condensation on a detecting element and on a temperature compensation element of a detector section.

Priority is claimed on Japanese Patent Application No. 2002-139094, the content of which is incorporated herein by reference.

BACKGROUND OF THE INVENTION

Conventionally, for example, a solid high-polymer membrane-type fuel cell is provided with a cell wherein a solid high-polymer electrolytic membrane is sandwiched between a fuel electrode and an oxygen electrode, and a plurality of cells are configured in a layered stack (hereafter referred to as a fuel cell). Hydrogen is supplied to the fuel electrode as fuel, and air is supplied to the oxygen electrode as oxidant, and oxygen ions produced at the fuel electrode due to a catalytic reaction pass through the solid high-polymer electrolytic membrane and migrate to the oxygen electrode, so that electricity is generated by an electrochemical reaction with oxygen at the oxygen electrode.

In fuel cells such as this solid high-polymer membrane-type fuel cell, conventionally there is known a protective apparatus which is provided with a hydrogen detector (gas sensor) in the exhaust system, for example on the oxygen electrode side of the fuel cell, and if this hydrogen detector detects leakage of hydrogen from the fuel electrode through the solid high-polymer electrolytic membrane to the oxygen electrode, it shuts off the supply of fuel (refer for example to Japanese Unexamined Patent Application, First Publication No. H06-223850).

Furthermore, as the hydrogen detector there is known a gas-contact combustion-type hydrogen detector which is provided with a gas detection element including for example a catalyst of platinum or the like, and a temperature compensation element as a pair. This hydrogen detector detects the concentration of hydrogen gas according to a difference in electrical resistance which occurs between a condition of the temperature compensation element for when the gas detection element becomes relatively hot due to heat produced by combustion when hydrogen contacts the catalyst of platinum or the like, and a condition at a relatively low temperature such as under ambient temperature.

Incidentally, in the fuel cell of the solid high-polymer membrane-type fuel cell and the like as described above, in order to maintain the ion conductivity of the solid high-polymer electrolytic membrane, water (humidifying water) is mixed with the reactant gas (for example, hydrogen or air) supplied to the fuel cell, with a humidifier or the like. Moreover, since reaction-generated water is produced by the electrochemical reaction when the fuel cell is in operation, the fuel cell exhaust gas, particularly the exhaust gas from oxygen electrode, is a high-humidity gas.

Therefore, in the protective apparatus of the fuel cell according to one example of the aforementioned conventional technology, due to the highly humid off-gas discharged from the fuel cell, condensation may occur on the hydrogen detector and the like, positioned in the flow path of the off-gas. In this case, deterioration of, and damage to, the hydrogen detector may occur. In particular, in the solid high-polymer membrane-type fuel cell, the normal operating temperature is lower than the evaporation temperature of water, so that the off-gas is highly humid and a gas having a high water content is discharged. Therefore there is the problem that the moisture content of the off-gas readily condenses.

Furthermore, for example, when the gas-contact combustion-type hydrogen detector is provided, particularly when provided in the exhaust system on the oxygen electrode side of the fuel cell, if electricity is supplied to the gas detection element while humidifying water or reaction-generated water and the like is adhered to it, localized non-uniformities in temperature distribution occur on the surface of the element, and may result in damage to, and decreased sensitivity of, the element.

SUMMARY OF THE INVENTION

The present invention addresses the aforementioned problems, with an object of providing a method of starting, stopping, and operating, a gas sensor with a built-in heater, wherein it is possible to prevent damage to, deterioration of, and reduction in accuracy of detection of, the gas sensor.

In order to resolve the aforementioned problems and achieve the related object, a method of starting a gas sensor with a built-in heater of a first aspect of the present invention, in a method of starting a gas sensor with a built-in heater (e.g., the gas sensor 15 in the embodiment described below) which is provided with: a flow tube in which a detection gas flows (e.g., the outlet side pipe 14 in the embodiment described below); a gas detection chamber into which the detection gas is introduced (e.g., the gas detection chamber 24 in the embodiment described below) provided in the flow tube; and a heater which heats the interior of the gas detection chamber (e.g., the heater 27 in the embodiment described below), and which detects the detection gas, is characterized by starting operation of the heater prior to starting operation of the gas sensor with a built-in heater.

According to the aforementioned method of starting a gas sensor with a built-in heater, by starting operation of the heater prior to starting operation of the gas sensor with a built-in heater, the gas sensor with a built-in heater can be started in a state wherein the occurrence of condensation has been prevented.

Moreover, a method of starting a gas sensor with a built-in heater in a second aspect of the present invention is characterized by detecting the temperature inside the gas detection chamber (e.g., step S14 and step S16 in the embodiment described below), and starting the heater, and then starting the gas sensor with a built-in heater when the temperature inside the gas detection chamber exceeds a predetermined threshold temperature.

According to the aforementioned method of starting a gas sensor with a built-in heater, by setting the temperature inside the gas detection chamber higher than the predetermined threshold temperature, the gas sensor with a built-in heater can be started in a state wherein the occurrence of condensation has been reliably prevented.

Furthermore, in a method of starting a gas sensor with a built-in heater in a third aspect of the present invention, the detection gas is hydrogen gas contained within off-gas discharged from an oxygen electrode of a fuel cell, and the method is characterized by flowing the off-gas through the flow tube after starting operation of the gas sensor with a built-in heater.

According to the aforementioned method of starting a gas sensor with a built-in heater, by starting the flow of cathode off-gas of the fuel cell to the flow tube at or after operation of the gas sensor with a built-in heater, the occurrence of missed detection and the like with respect to the hydrogen gas within the cathode off-gas can be reliably prevented.

Moreover, a method of starting a gas sensor with a built-in heater in a fourth aspect of the present invention, in a method of starting a gas sensor with a built-in heater which is provided with: a gas detection chamber provided in an off-gas pipe (e.g., the outlet pipe 14 in the embodiment described below) through which off-gas discharged from an oxygen electrode of a fuel cell flows, into which hydrogen gas contained in the off-gas is introduced as detection gas; and a heater which heats the interior of the gas detection chamber, and which detects the detection gas, is characterized by starting operation of the gas sensor with a built-in heater and the heater prior to starting flow of the off-gas.

According to the aforementioned method of starting a gas sensor with a built-in heater, by flowing the off-gas after starting the gas sensor with a built-in heater, the occurrence of missed detection and the like with respect to the hydrogen gas flowing through the off-gas piping can be suppressed while preventing condensation on the gas sensor with a built-in heater, particularly due to off-gas from a high-humidity fuel cell.

Furthermore, in a method of starting a gas sensor with a built-in heater in a fifth aspect of the present invention, the gas sensor with a built-in heater is a gas-contact combustion-type gas sensor which is provided with a detection element furnished with a catalyst, and a temperature compensation element, inside the gas detection chamber, and which detects the concentration of the hydrogen gas in accordance with a difference in the electrical resistance value between the gas detection element and the temperature compensation element, produced due to heat produced by combustion when hydrogen contained in the off-gas contacts the catalyst, and the method is characterized by starting supply of electricity to the detection element, the temperature compensation element, and the heater prior to starting flow of the off-gas.

According to the aforementioned method of starting a gas sensor with a built-in heater, by flowing the off-gas after starting supply of electricity to the detection element and the temperature compensation element, the occurrence of missed detection and the like with respect to the hydrogen gas flowing through the off-gas piping can be suppressed while preventing condensation on the gas sensor with a built-in heater particularly due to off-gas from a high-humidity fuel cell.

Moreover, a method of starting a gas sensor with a built-in heater in a sixth aspect of the present invention is characterized by synchronizing starting supply of electricity to the heater, with starting supply of electricity to the detection element and the temperature compensation element.

According to the aforementioned method of starting a gas sensor with a built-in heater, by synchronizing the timing of starting supply of electricity to the detection element and the temperature compensation element, with the starting of supply of electricity to the heater, then for example, by setting to the same time or the like, the gas sensor with a built-in heater can be started in a state wherein the occurrence of condensation on the detection element and the temperature compensation element is prevented, while preventing an increase in electric power consumption due to starting supply of electricity to the heater too early, for example under a low-humidity environment. Furthermore, control when starting the heater and the gas sensor with a built-in heater can be simplified.

Moreover, a method of starting a gas sensor with a built-in heater in a seventh aspect of the present invention is characterized by starting supply of electricity to the heater prior to starting supply of electricity to the detection element and the temperature compensation element.

According to the aforementioned method of starting a gas sensor with a built-in heater, the gas sensor with a built-in heater can be started in a state wherein the occurrence of condensation on the detection element and the temperature compensation element is reliably prevented.

Furthermore, a method of starting a gas sensor with a built-in heater in an eighth aspect of the present invention, is a method of starting a gas sensor with a built-in heater provided with a detection element furnished with a catalyst, and a temperature compensation element, inside the gas detection chamber into which the detection gas is introduced, and a heater capable of changing the humidity state inside the gas detection chamber, the method being characterized by starting supply of electricity to the heater prior to starting supply of electricity to the detection element and the temperature compensation element, to thereby reduce the relative humidity inside the gas detection chamber.

According to the aforementioned method of starting a gas sensor with a built-in heater, the supply of electricity to the detection element and the temperature compensation element can be started after reliably reducing the relative humidity inside the gas detection chamber. Therefore supply of electricity to each element in a state where condensation has occurred on the catalyst and the like of the detection element can be prevented, and the gas sensor with a built-in heater can be started in a state wherein the occurrence of condensation on the detection element and the temperature compensation element inside the gas detection chamber has been prevented.

Moreover, a method of stopping a gas sensor with a built-in heater in a ninth aspect of the present invention, in a method of stopping a gas sensor with a built-in heater (e.g., the gas sensor 15 in the embodiment described below) which is provided with: a flow tube in which a detection gas flows (e.g., the outlet side pipe 14 in the embodiment described below); a gas detection chamber into which the detection gas is introduced (e.g., the gas detection chamber 24 in the embodiment described below) provided in the flow tube; and a heater (e.g., the heater 27 in the embodiment described below) which heats the interior of the gas detection chamber, and which detects the detection gas, is characterized by stopping operation of the gas sensor with a built-in heater prior to stopping operation of the heater.

According to the aforementioned method of stopping a gas sensor with a built-in heater, by stopping operation of the gas sensor with a built-in heater prior to stopping operation of the heater, then for example, in preparation for restart or the like of the gas sensor with a built-in heater, the heater can be stopped in a state wherein the occurrence of condensation has been prevented.

Furthermore, a method of stopping a gas sensor with a built-in heater in a tenth aspect of the present invention is characterized by: detecting the temperature inside the gas detection chamber and the temperature of the detection gas on an upstream side of the gas sensor with a built-in heater (e.g., step S14 and step S16 in the embodiment described below); stopping operation of the gas sensor with a built-in heater prior to stopping operation of the heater; and then in a state wherein the temperature inside the gas detection chamber has become a value of a predetermined temperature range which is higher than the temperature of the detection gas on the upstream side of the gas sensor with a built-in heater, stopping operation of the heater after a predetermined time has elapsed.

According to the aforementioned method of stopping a gas sensor with a built-in heater, by setting the temperature inside the gas detection chamber to a value of a predetermined temperature range which is higher than the temperature of the detection gas, the heater can be stopped in a state wherein the occurrence of condensation is reliably prevented.

Moreover, in a method of stopping a gas sensor with a built-in heater in an eleventh aspect of the present invention, the detection gas is hydrogen gas contained in the off-gas discharged from an oxygen electrode of a fuel cell, and the method is characterized by flowing the off-gas through the flow tube at least until after stopping operation of the gas sensor with a built-in heater.

According to the aforementioned method of stopping a gas sensor with a built-in heater, moisture within the flow tube can be removed by the flow of off-gas, and the occurrence of condensation on the gas sensor with a built-in heater while stopped, can be better prevented.

Furthermore, a method of stopping a gas sensor with a built-in heater in a twelfth aspect of the present invention, in a method of stopping a gas sensor with a built-in heater which is provided with: a gas detection chamber provided in an off-gas pipe (e.g., the outlet pipe 14 in the embodiment described below) through which off-gas discharged from an oxygen electrode of a fuel cell flows, into which hydrogen gas contained in the off-gas is introduced as detection gas; and a heater which heats the interior of the gas detection chamber, and which detects the detection gas, is characterized by stopping the flow of the off-gas prior to stopping the operation of the gas sensor with a built-in heater, and the heater.

According to the aforementioned method of stopping a gas sensor with a built-in heater, by stopping the gas sensor with a built-in heater after stopping the flow of off-gas, the occurrence of missed detection and the like with respect to the hydrogen gas flowing through the off-gas piping can be suppressed while preventing condensation on the gas sensor with a built-in heater, particularly due to off-gas from a high-humidity fuel cell. Moreover, since the relative humidity inside the gas detection chamber can be decreased beforehand in preparation for the next start, a state wherein condensation occurs on the gas sensor with a built-in heater at the time of the next start can be prevented.

Furthermore, in a method of stopping a gas sensor with a built-in heater in a thirteenth aspect of the present invention, the gas sensor with a built-in heater is a gas-contact combustion-type gas sensor which is provided with a detection element furnished with a catalyst, and a temperature compensation element, inside the gas detection chamber, and which detects the concentration of the hydrogen gas in accordance with a difference in an electrical resistance value between the gas detection element and the temperature compensation element, produced due to heat produced by combustion when hydrogen contained in the off-gas contacts the catalyst, and the method is characterized by stopping the flow of the off-gas prior to stopping supply of electricity to the detection element and the temperature compensation element.

According to the aforementioned method of stopping a gas sensor with a built-in heater, by stopping supply of electricity to the detection element and the temperature compensation element after stopping the flow of off-gas, the occurrence of missed detection and the like with respect to the hydrogen gas flowing through the off-gas piping can be suppressed while preventing condensation on the gas sensor with a built-in heater, particularly due to off-gas from a high-humidity fuel cell. Moreover, since the relative humidity inside the gas detection chamber can be decreased in preparation for the next start, a state wherein condensation occurs on the gas sensor with a built-in heater at the time of the next start can be prevented.

Furthermore, a method of stopping a gas sensor with a built-in heater in a fourteenth aspect of the present invention is characterized by synchronizing stopping flow of electricity to the heater, with stopping supply of electricity to the detection element and the temperature compensation element.

According to the aforementioned method of stopping a gas sensor with a built-in heater, by synchronizing the timing of stopping supply of electricity to the detection element and the temperature compensation element, with the stopping of supply of electricity to the heater, then for example, by setting the same time or the like, the heater can be stopped in a state wherein the occurrence of condensation on the detection element and the temperature compensation element has been prevented for example in preparation for the next start of the gas sensor with a built-in heater, while preventing an increase in electric power consumption due to stopping supply of electricity to the heater too late, for example, under a low-humidity environment. Furthermore, control when stopping the heater and the gas sensor with a built-in heater can be simplified.

Moreover, a method of stopping a gas sensor with a built-in heater in a fifteenth aspect of the present invention is characterized by stopping supply of electricity to the detection element and the temperature compensation element prior to stopping supply of electricity to the heater.

According to the aforementioned method of stopping a gas sensor with a built-in heater, the heater can be stopped in a state wherein the occurrence of condensation on the detection element and the temperature compensation element is reliably prevented, in preparation for restart or the like of the gas sensor with a built-in heater.

Moreover, a method of stopping a gas sensor with a built-in heater in a sixteenth aspect of the present invention is a method of stopping a gas sensor with a built-in heater provided with a detection element furnished with a catalyst, and a temperature compensation element, inside a gas detection chamber into which a detection gas is introduced, and a heater capable of changing the humidity state inside the gas detection chamber, the method being characterized by continuing supply of electricity to the heater for a predetermined time, after stopping supply of electricity to the detection element and the temperature compensation element, and stopping supply of electricity to the heater after the predetermined time has elapsed, to thereby decrease in advance the relative humidity inside the gas detection chamber for at the time of starting a next operation.

According to the aforementioned method of stopping a gas sensor with a built-in heater, the gas sensor with a built-in heater can be stopped in a state wherein the occurrence of condensation on the detection element and the temperature compensation element inside the gas detection chamber has been prevented. Furthermore, since the relative humidity inside the gas detection chamber can be decreased in advance ready for at the time of the next start, a state wherein condensation occurs on the gas sensor with a built-in heater at the time of the next start can be prevented, and the time required for starting can be shortened.

Moreover, a method of operating a gas sensor with a built-in heater in a seventeenth aspect of the present invention, in a method of operating a gas sensor with a built-in heater which is provided with: a gas detection chamber provided in an off-gas pipe (e.g., the outlet pipe 14 in the embodiment described below) through which off-gas discharged from an oxygen electrode of a fuel cell flows, into which hydrogen gas contained in the off-gas is introduced as detection gas; and a heater which heats the interior of the gas detection chamber, and which detects the detection gas, is characterized by: starting supply of electricity to the gas sensor with a built-in heater and to the heater prior to starting the flow of the off-gas, when starting operation of the fuel cell; continuing supply of electricity to the gas sensor with a built-in heater and to the heater during normal operation of the fuel cell; and stopping the flow of the off-gas prior to stopping supply of electricity to the gas sensor with a built-in heater and to the heater when operation of the fuel cell is stopped.

According to the aforementioned method of operating a gas sensor with a built-in heater, the gas sensor with a built-in heater can be started in a state wherein the occurrence of condensation inside the gas detection chamber has been prevented, while suppressing the occurrence of missed detection and the like with respect to the hydrogen gas flowing in the off-gas pipe. Furthermore, the occurrence of condensation inside the gas detection chamber can also be prevented during normal operation of the fuel cell. Moreover, the gas sensor with a built-in heater can be stopped in a state wherein the occurrence of condensation inside the gas detection chamber has been prevented in preparation for, for example, restart and the like of the gas sensor with a built-in heater, while suppressing the occurrence of missed detection and the like with respect to the hydrogen gas flowing in the off-gas pipe.

Furthermore, since the heater is in continuous operation while the fuel cell is in operation, the occurrence of condensation on the gas sensor with a built-in heater can be reliably prevented, and the occurrence of missed detection and the like of the hydrogen gas can be suppressed.

Moreover, a method of operating a gas sensor with a built-in heater in an eighteenth aspect of the present invention is characterized by maintaining a temperature inside the gas detection chamber of the gas sensor with a built-in heater within a predetermined temperature range, by controlling an amount of electricity supplied to the heater during normal operation of the fuel cell.

According to the aforementioned method of operating a gas sensor with a built-in heater, by controlling the amount of electricity supplied to the heater by, for example feedback control of the value of the current value supplied to the heater, or by chopper control of the supplied electricity based for example on on/off operation of a switching element, and maintaining the temperature inside the gas detection chamber within a predetermined temperature range, then the occurrence of condensation inside the gas detection chamber due to the changing temperature inside the gas detection chamber can be reliably prevented.

Furthermore, a method of operating a gas sensor with a built-in heater in a nineteenth aspect of the present invention is characterized by temporarily increasing the temperature inside the gas detection chamber of the gas sensor with a built-in heater to a temperature greater than the predetermined temperature range, when stopping operation of the fuel cell.

According to the aforementioned method of operating a gas sensor with a built-in heater, for example, even when the amount of off-gas flowing inside the off-gas pipe is increased and purging is executed to discharge moisture remaining in the fuel cell and the like to the outside, by temporarily increasing the temperature inside the gas detection chamber, the amount of saturated water vapor is increased, and the occurrence of condensation inside the gas detection chamber can be prevented, and the time for which the electricity is supplied continuously to the heater while operation is stopped can be shortened.

Furthermore, a method of operating a gas sensor with a built-in heater in a twentieth aspect of the present invention is characterized by increasing or decreasing the amount of electricity supplied to the heater in accordance with the load state of the fuel cell, during normal operation of the fuel cell.

According to the aforementioned method of operating a gas sensor with a built-in heater, even when the amount of off-gas flowing in the off-gas pipe changes in accordance with the load state of the fuel cell, and the humidity state inside the gas detection chamber changes due to the moisture content in the off-gas which changes due to changes in the amount of off-gas, that is to say, the load state of the fuel cell, the occurrence of condensation inside the gas detection chamber can be prevented, by maintaining the humidity state inside the gas detection chamber in a predetermined state.

Furthermore, a method of operating a gas sensor with a built-in heater in a twenty-first aspect of the present invention is characterized by increasing the amount of electricity supplied to the heater accompanying a load state of the fuel cell reaching a high-load state.

According to the aforementioned method of operating a gas sensor with a built-in heater, even when accompanying the load state of the fuel cell reaching a high-load state, for example, the amount of off-gas flowing in the off-gas pipe increases and the temperature of the gas detection chamber exposed to the off-gas decreases, and for example, the amount of produced water contained in the off-gas increases and the relative humidity inside the gas detection chamber increases, the occurrence of condensation inside the gas detection chamber can be prevented by increasing the amount of electricity supplied to the heater to increase the temperature inside the gas detection chamber.

Moreover, a method of operating a gas sensor with a built-in heater in a twenty-second aspect of the present invention is a method of operating a gas sensor with a built-in heater provided with a detection element furnished with a catalyst, and a temperature compensation element, inside a gas detection chamber into which a detection gas is introduced and a heater capable of changing the humidity state inside the gas detection chamber, the method being characterized by: firstly starting supply of electricity to the heater when starting operation of the gas sensor with a built-in heater; and next starting supply of electricity to the detection element and the temperature compensation element after the relative humidity inside the gas detection chamber has decreased; continuing the supply of electricity to the heater during operation of the gas sensor with a built-in heater; and firstly stopping supply of electricity to the detection element and the temperature compensation element when stopping operation of the gas sensor with a built-in heater; and next stopping supply of electricity to the heater after the relative humidity inside the gas detection chamber has been decreased by continuing supply of electricity to the heater.

According to the aforementioned method of operating a gas sensor with a built-in heater, the gas sensor with a built-in heater can be started in a state wherein the occurrence of condensation inside the gas detection chamber has been prevented, while suppressing the occurrence of missed detection and the like with respect to the hydrogen gas flowing in the off-gas pipe. Furthermore, the occurrence of condensation inside the gas detection chamber can also be prevented during operation of the fuel cell. Moreover, the gas sensor with a built-in heater can be stopped in a state wherein the occurrence of condensation inside the gas detection chamber has been prevented in preparation for, for example, restart and the like of the gas sensor with a built-in heater, while suppressing the occurrence of missed detection and the like with respect to the hydrogen gas flowing in the off-gas pipe.

BRIEF DESCRIPTION OF THE DRAWINGS

FIG. 5 is a flowchart showing a method of starting a gas sensor with a built-in heater when an automobile ignition switch is turned ON.

FIG. 9 is a timing chart showing the state of the heater and the gas sensor, and the state of flow of off-gas, when the automobile ignition switch is turned ON.

DETAILED DESCRIPTION OF THE ILLUSTRATED EMBODIMENT

Hereunder is a description of a control apparatus for a gas sensor with a built-in heater, for implementing the methods of starting, stopping, and operating the gas sensor with a built-in heater according to one embodiment of the present invention, with reference to the drawings.

Figure 1:
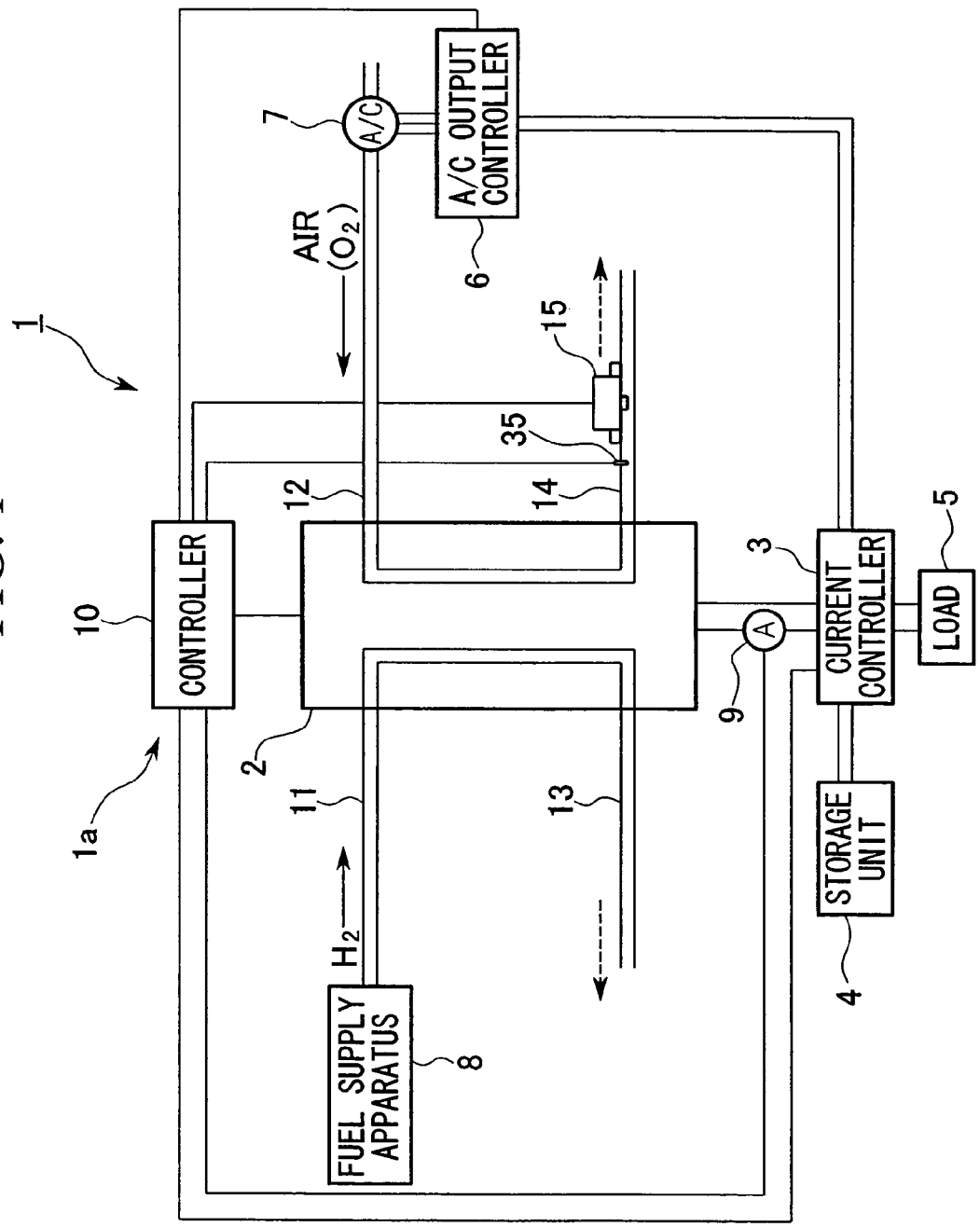
FIG. 1 is a block diagram of a fuel cell system provided with a control apparatus for a gas sensor with a built-in heater according to an embodiment of the present invention.
Figure 2:
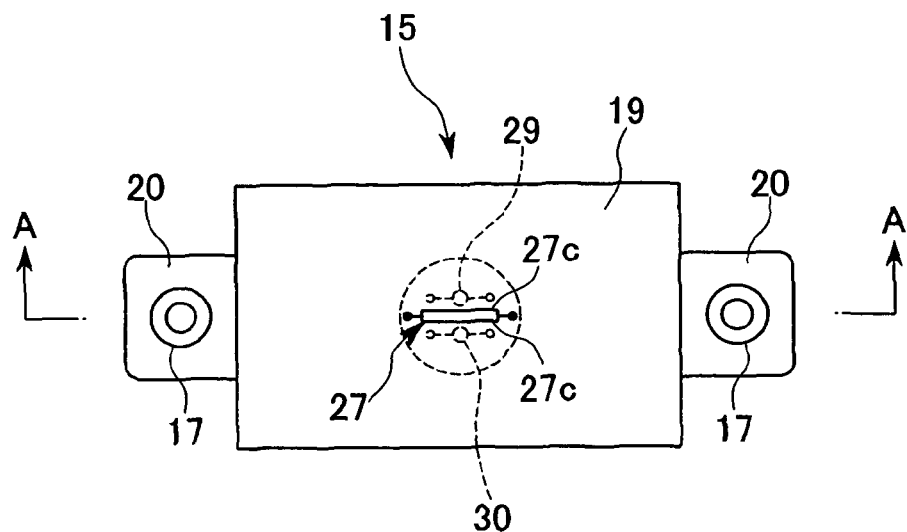
FIG. 2 is a plan view of the gas sensor of the embodiment of the present invention.
Figure 3:
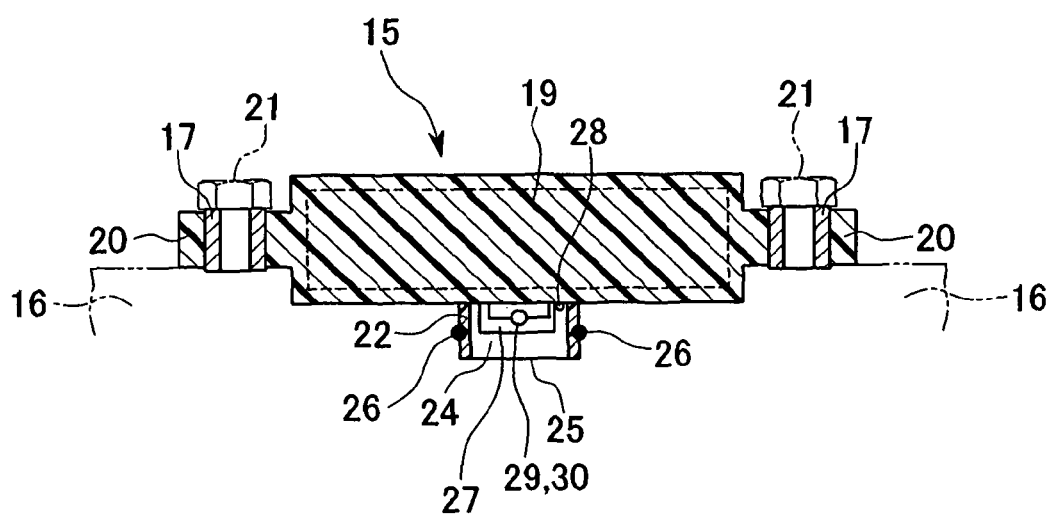
FIG. 3 is a simplified section view along the line A-A in FIG. 2.
Figure 4:
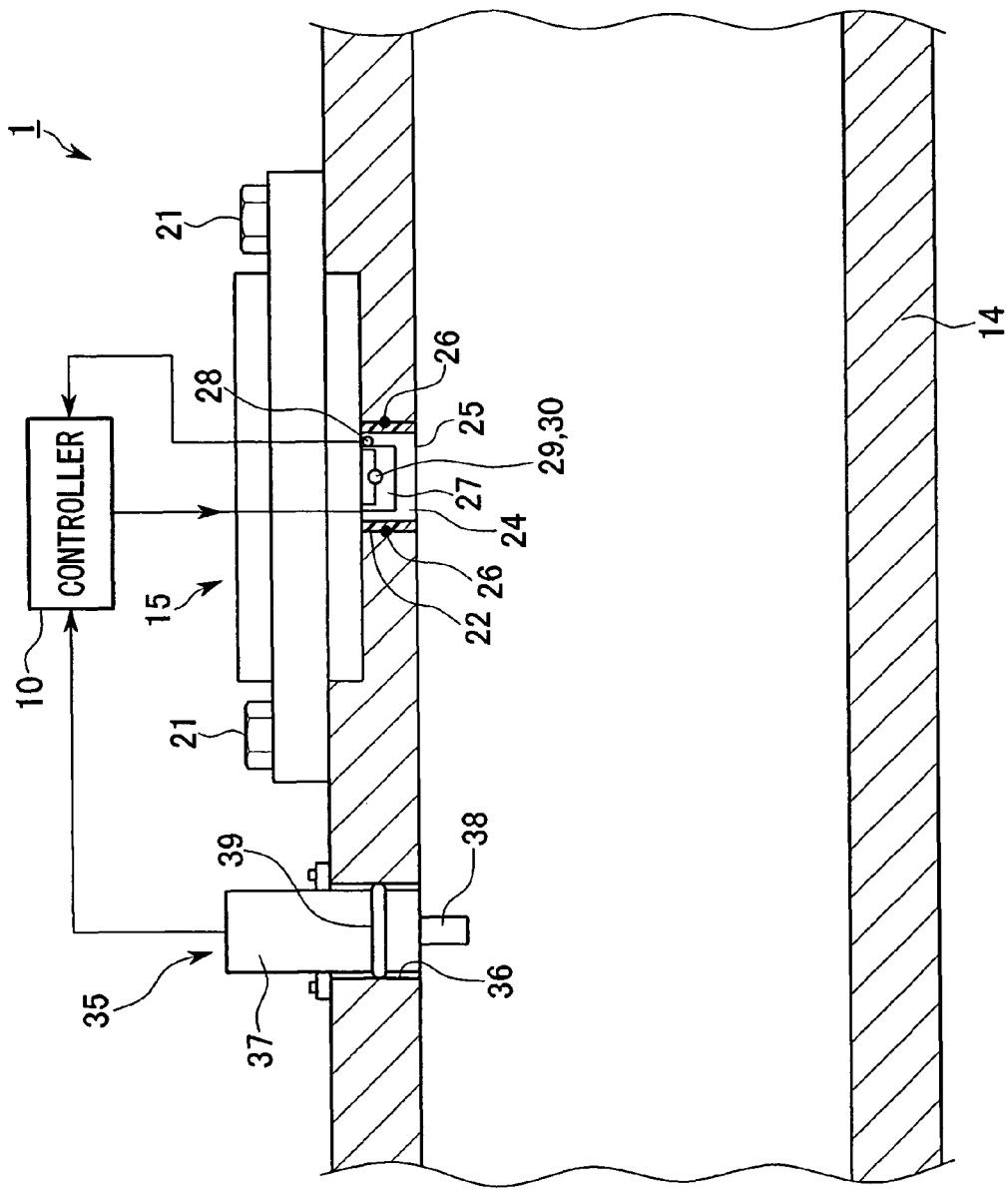
FIG. 4 is a block diagram of a control apparatus for the gas sensor with a built-in heater according to this embodiment of the present invention.

FIG. 1 is a block diagram of a fuel cell system provided with a control apparatus 1 for a gas sensor with a built-in heater, according to one embodiment of the present invention, FIG. 2 is a plan view of a gas sensor 15, FIG. 3 is a simplified section view along the line A-A in FIG. 2, and FIG. 4 is a block diagram of the control apparatus 1 for the gas sensor with a built-in heater according to an embodiment of the present invention.

As shown, for example, in FIG. 1, the control apparatus 1 for a gas sensor with a built-in heater, according to the present embodiment is one which in a fuel cell system 1a including: a fuel cell 2, a current controller 3, a storage unit 4, a load 5, an A/C output controller 6, an air compressor (A/C) 7, a fuel supply apparatus 8, an output current sensor 9, and a controller 10, controls starting, stopping, and operating of the gas sensor with a built-in heater (gas sensor) 15 provided in the oxygen electrode outlet pipe 14, of the pipes 11, 12, 13, and 14 connected to the fuel cell 2.

The fuel cell 2 is mounted in a vehicle as, for example, a power source for an electric vehicle or the like, and includes a plurality of layers of fuel cells, each fuel cell being an electrolytic electrode structure wherein a solid high-polymer electrolytic membrane is sandwiched between a hydrogen electrode and an oxygen electrode, and is further sandwiched between a pair of separators (not shown in drawings).

The inlet pipe 11 connected to the hydrogen electrode of the fuel cell 2 is supplied with fuel gas containing hydrogen gas from a fuel supply apparatus 8 provided with, for example, a high pressure hydrogen tank or the like, and ionized hydrogen from a catalytic reaction on a catalytic electrode of the hydrogen electrode migrates to the oxygen electrode via a suitably humidified solid high-polymer electrolytic membrane, and electrons generated accompanying this migration are extracted to an external circuit and used as direct current electrical energy. The inlet pipe 12 connected to the oxygen electrode is, for example, supplied with an oxidant gas such as oxygen or the like, or with air, from an air compressor (A/C) 7, and hydrogen ions, electrons, and oxygen are reacted on this electrode to produce water. Then the reacted so called off-gas from both the hydrogen electrode and the oxygen electrode is discharged from the system via the outlet pipes 13 and 14. In particular, the solid high-polymer electrolytic-type fuel cell normally operates below the evaporation temperature of water, and the off-gas is therefore highly humid, and a gas having a high water content is discharged.

Here, a gas sensor with a built-in heater (gas sensor) 15 of a gas-contact combustion-type, is fitted vertically in the outlet pipe 14 of the oxygen electrode, and this gas sensor enables verification that hydrogen is not discharged from the outlet pipe 14 of the oxygen electrode.

Furthermore, the air compressor 7, for example, takes air from outside the automobile and compresses it, and supplies this air to the oxygen electrode of the fuel cell 2 as reactant gas.

The speed of rotation of the motor (not shown in drawings) which drive this air compressor 7 is controlled based on control instructions input from the controller 10, by the A/C output controller 6 which is provided with, for example, a PWM (pulse width modulation) inverter using pulse width modulation.

The generated current (output current) extracted from the fuel cell 2 is input to the current controller 3. To this current controller 3 is connected, a storage unit 4 formed from a capacitor or the like including a plurality of capacitor cells formed from, for example, electric double layer capacitors or electrolytic capacitors and the like mutually connected in series.

The fuel cell 2, the current controller 3, and the storage unit 4 are connected in parallel to a load 5 formed from, for example, a propulsion motor (not shown in drawings) and various auxiliary equipment such as a cooling apparatus (not shown in drawings) of the fuel cell 2 and the storage unit 4, and an air conditioning apparatus (not shown in drawings), and the A/C output controller 6.

The controller 10 in this fuel cell system 1a outputs an instruction value for the amount of air supplied to the fuel cell 2 from the air compressor 7, and an instruction value for the amount of fuel gas supplied to the fuel cell 2 from the fuel supply apparatus 8 based on, for example, the operation state of the automobile, the concentration of the hydrogen contained in the fuel gas supplied to the hydrogen electrode of the fuel cell 2, the concentration of the hydrogen contained in the off-gas discharged from the hydrogen electrode of the fuel cell 2, the electricity generation state of the fuel cell 2, for example, the inter-terminal voltage of each of the plurality of fuel cells, and the output current extracted from the fuel cell 2, and controls the electricity generation state of the fuel cell 2.

Therefore the detection signal output from the output current sensor 9 which detects the current value of the output current extracted from the fuel cell 2, is input to the controller 10.

Moreover, the controller 10 controls the current value of the output current extracted from the fuel cell 2 using the current controller 3, based on the electricity generation instruction for the fuel cell 2 (FC output instruction value).

For example, as shown in FIG. 2, the gas sensor 15 is provided with a long rectangular-shaped case 19 along the length of the outlet pipe 14. The case 19 is made for example from polyphenylene sulfide, and is provided with flange parts 20 at both ends in the length direction. A collar 17 is fitted to each flange part 20, and for example as shown in FIG. 3, a bolt 21 is inserted through each collar 17 and tightened into a mount 16 of the outlet pipe 14 to secure the flange.

For example, as shown in FIG. 3, on the bottom face of the case 19 is formed a cylindrical part 22 which is inserted from the outside into a through-hole 18 in the outlet pipe 14. A circuit board (not shown in drawings) is provided inside the case 19. A detection element 29 and a temperature compensation element 30 described later are connected to this circuit board. The interior of the cylindrical part 22 is formed as a gas detection chamber 24, and the inside of the cylindrical part 22 is formed open as a gas introduction part 25.

Furthermore, a seal member 26 is fitted to the outer peripheral face of the cylindrical part 22, and is in close contact with the inner peripheral wall of the through-hole 18 to maintain airtightness. The detection element 29 and the temperature compensation element 30 are mounted inside the cylindrical part 22.

The detection element 29 and the temperature compensation element 30 are connected to the circuit board and are provided as a pair at the same height and separated by a predetermined spacing, inside the gas detection chamber 24.

The detection element 29 is a well-known device, being a gas-contact combustion-type gas sensor which employs the heat of combustion when hydrogen being the detection gas contacts a catalyst such as platinum or the like, and employs the difference in electrical resistance produced between the gas detection element 29 which reaches a higher temperature due to combustion of the hydrogen, and the temperature compensation element 30 at ambient temperature, to detect the concentration of hydrogen.

Here, for example, as shown in FIG. 2, inside the gas detection chamber 24 a rectangular plate-shaped heater 27 which is upstanding in the direction of flow of detection gas, is positioned between the detection element 29 and the temperature compensation element 30 so as to block off between the two. This heater 27 includes a resistor or the like, and is supplied with electricity by the circuit board to heat the interior of the gas detection chamber 24, and is positioned with its heat-radiating faces 27C oriented towards the detection element 29 and the temperature compensation element 30. That is to say, each face of the heater 27 is formed as a heat-radiating face 27C. By means of the heater 27, the detection gas which flows in is distributed uniformly between the detection element 29 and the temperature compensation element 30.

Moreover, a temperature sensor 28 is fitted in the gas detection chamber 24 to detect the temperature inside the gas detection chamber 24.

In this manner, in the outlet pipe 14 on the oxygen electrode outlet side wherein the gas sensor 15 is fitted, a temperature sensor 35 is fitted to detect the temperature of the detection gas upstream and adjacent to the mounting position of the gas sensor 15, that is to say, the gas temperature on the upstream side of the gas sensor 15.

The base part 37 of the temperature sensor 35 is fixed in and passes through a through-hole 36 formed in the outlet pipe 14, and a detector part 38 at the tip is inserted into the outlet pipe 14. A seal member 39 is fitted to the peripheral wall of the base part 37 of the temperature sensor 35, to maintain a seal between the temperature sensor 35 and the through-hole 36.

Here, the controller 10 is connected to the temperature sensor 35 fitted to the outlet pipe 14, and the temperature sensor 28 provided inside the gas sensor 15, and is also connected to the heater 27 of the gas sensor 15.

The controller 10 controls the operation state of the gas sensor 15 and heater 27, for example, the timing of starting and stopping, and the electricity supply state for the detection element 29, the temperature compensation element 30, and the heater 27, in accordance with the operation state and the like of the fuel cell 2.

For example, as described below, the controller 10 controls the supply of electricity to the heater 27 based on the detected temperatures of the temperature sensors 28 and 35, and for example, controls the temperature inside the gas detection chamber 24 detected by the temperature sensor 28 to within a predetermined temperature range during operation and the like of the fuel cell 2.

Furthermore, as described below, the controller 10 controls the supply of electricity to the heater 27 so that the temperature inside the gas detection chamber 24 detected by the temperature sensor 28 becomes a temperature greater than a predetermined temperature #Ti at start, when the gas sensor 15 is started in association with, for example, starting of the fuel cell 2. Moreover, it controls the supply of electricity to the heater 27 so as to ensure that the difference between the temperature inside the gas detection chamber 24 (for example, the gas temperature inside the gas detection chamber 24) detected by the temperature sensor 28, and the gas temperature upstream of the gas sensor 15 detected by the temperature sensor 35, when the gas sensor 15 is stopped in association with for example, stopping the fuel cell 2, is within the predetermined temperature range.

At this time, the controller 10 controls the amount of electricity supplied to the heater 27 by means of for example, feedback control of the current value of the electricity supplied to the heater 27, or for example, chopper control (that is to say, electricity on/off switching control) based on on/off operation or the like of a switching element.

Furthermore, as described below, in addition to the temperature state of the interior of the gas detection chamber 24 detected by the temperature sensor 28, during operation of the fuel cell 2, the controller 10 controls the amount of electricity supplied to the heater 27 in accordance with the electricity generation state of the fuel cell 2 calculated based on, for example, the load state of the fuel cell 2 during operation of the fuel cell 2, for example, the electricity generation instruction for the fuel cell 2 (FC output instruction value), for example, the value of the output current of the fuel cell 2 detected by the output current sensor 9, and for example, the detected value or the like of the flow of air supplied to the fuel cell 2 from the air compressor 7 detected by the flow sensor (not shown in drawings).

For example, when the load state of the fuel cell 2 changes to a high-load state, and there is a possibility of, for example, an increase in the amount of off-gas flowing in the outlet pipe 14 and a decrease in the temperature inside the gas detection chamber 24 of the gas sensor 15 exposed to the off-gas, the controller 10 can prevent the occurrence of condensation inside the gas detection chamber 24 by increasing the amount of electricity supplied to the heater 27 to increase the temperature inside the gas detection chamber 24. On the other hand, when the load state of the fuel cell 2 changes to a low-load state, the controller 10 decreases the amount of electricity supplied to the heater 27 and thus suppresses excess energy consumption.

Moreover, as described below, in addition to the temperature state of the interior of the gas detection chamber 24 detected by the temperature sensor 28, the controller 10 controls the amount of electricity supplied to the heater 27 in accordance with, for example, the operation state of the fuel cell 2 (that is to say, the operation state including starting and stopping of the fuel cell 2).

For example, when the fuel cell 2 is stopped, and for example, when the amount of off-gas flowing in the outlet pipes 13 and 14 is increased, and a purge operation is executed to discharge to the outside water remaining in the fuel cell system 1a and the like, the controller 10 increases the amount of saturated water vapor in the atmosphere gas inside the gas detection chamber 24 by temporarily increasing the temperature in the gas detection chamber 24, and thus prevents the occurrence of condensation inside the gas detection chamber 24.

Here, for example, when the fuel cell 2 is started, the controller 10 starts the supply of electricity to the gas sensor 15, that is to say, the detection element 29 and the temperature compensation element 30, and to the heater 27, prior to starting the flow of off-gas inside the outlet pipe 14.

For example, during operation of the fuel cell 2, the controller 10 continues the supply of electricity supplied to the heater 27 by feedback control of the current value of the electricity supplied to the heater 27, or for example, chopper control (that is to say, electricity on/off switching control) based on on/off operation or the like of the switching element in accordance with, for example, the load state or operation state of the fuel cell 2.

Then for example, when the fuel cell 2 is stopped, the controller 10 stops the flow of off-gas in the outlet pipe 14, and then stops the supply of electricity to the gas sensor 15, that is to say, the detection element 29 and the temperature compensation element 30, and to the heater 27.

Furthermore, as described below, in addition to the temperature state of the interior of the gas detection chamber 24 detected by the temperature sensor 28, the controller 10 controls the timing of starting and stopping supply of electricity to the heater 27 based on, for example, the detected value of relative humidity output from the humidity sensor (not shown in drawings) which detects relative humidity inside the gas detection chamber 24, or for example, a lookup value for relative humidity obtained from a previously created relative humidity map or the like corresponding to the temperature state inside the gas detection chamber 24.

For example, when the gas sensor 15 is started, the controller 10 first starts supply of electricity to the heater 27, and when the relative humidity inside the gas detection chamber 24 decreases to the predetermined humidity state, starts supply of electricity to the detection element 29 and the temperature compensation element 30. On the other hand, when operation of the gas sensor 15 is stopped, the controller 10 stops supply of electricity to the detection element 29 and the temperature compensation element 30, and after the relative humidity inside the gas detection chamber 24 has decreased to the predetermined humidity state, stops supply of electricity to the heater 27.

The control apparatus 1 for a gas sensor with a built-in heater according to the present embodiment includes, for example, the gas sensor 15, the temperature sensor 35, and the controller 10.

Hereunder is a description of the methods of starting, stopping, and operating a gas sensor with a built-in heater employing the control apparatus 1 for a gas sensor with a built-in heater, with reference to the drawings.

Figure 5:
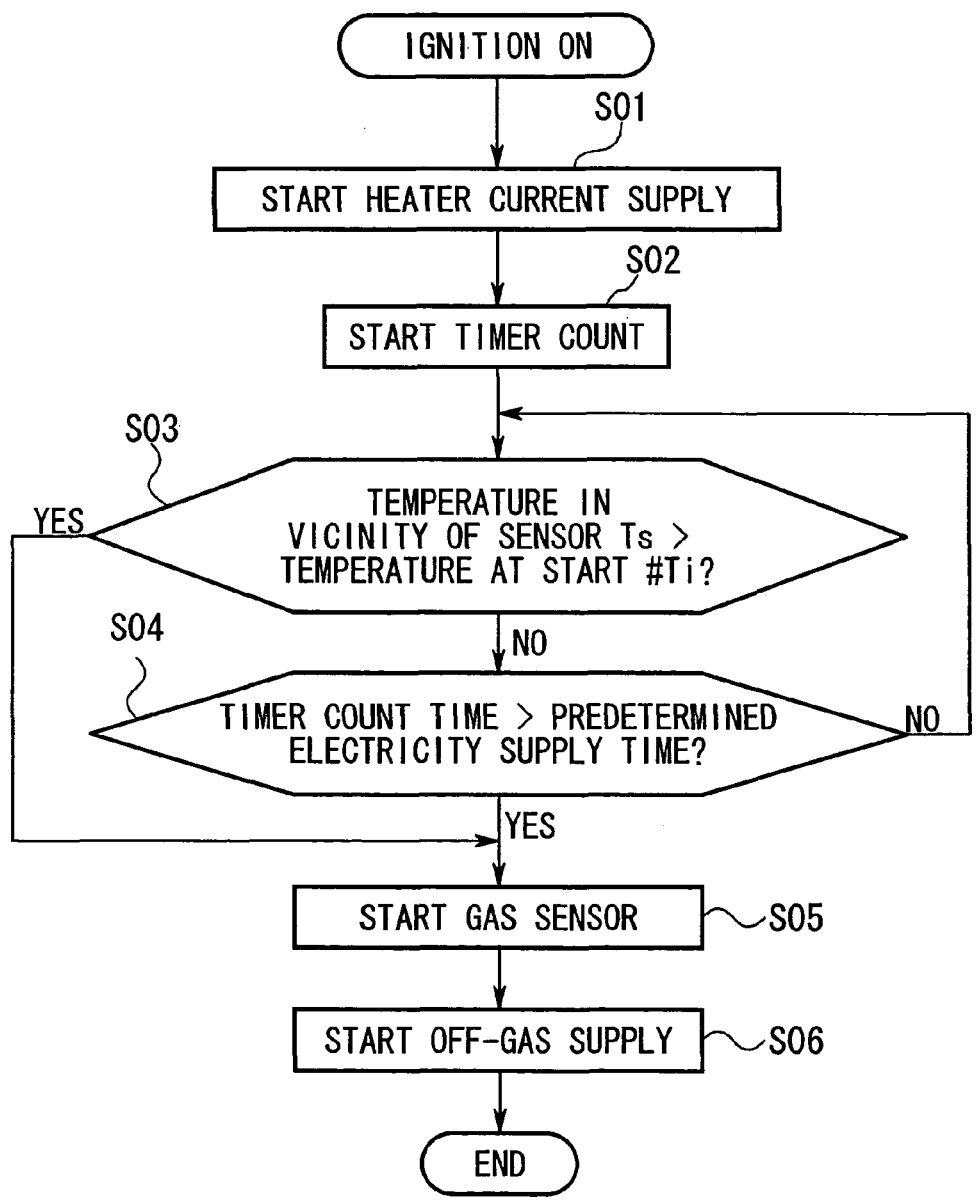
Figure 6:
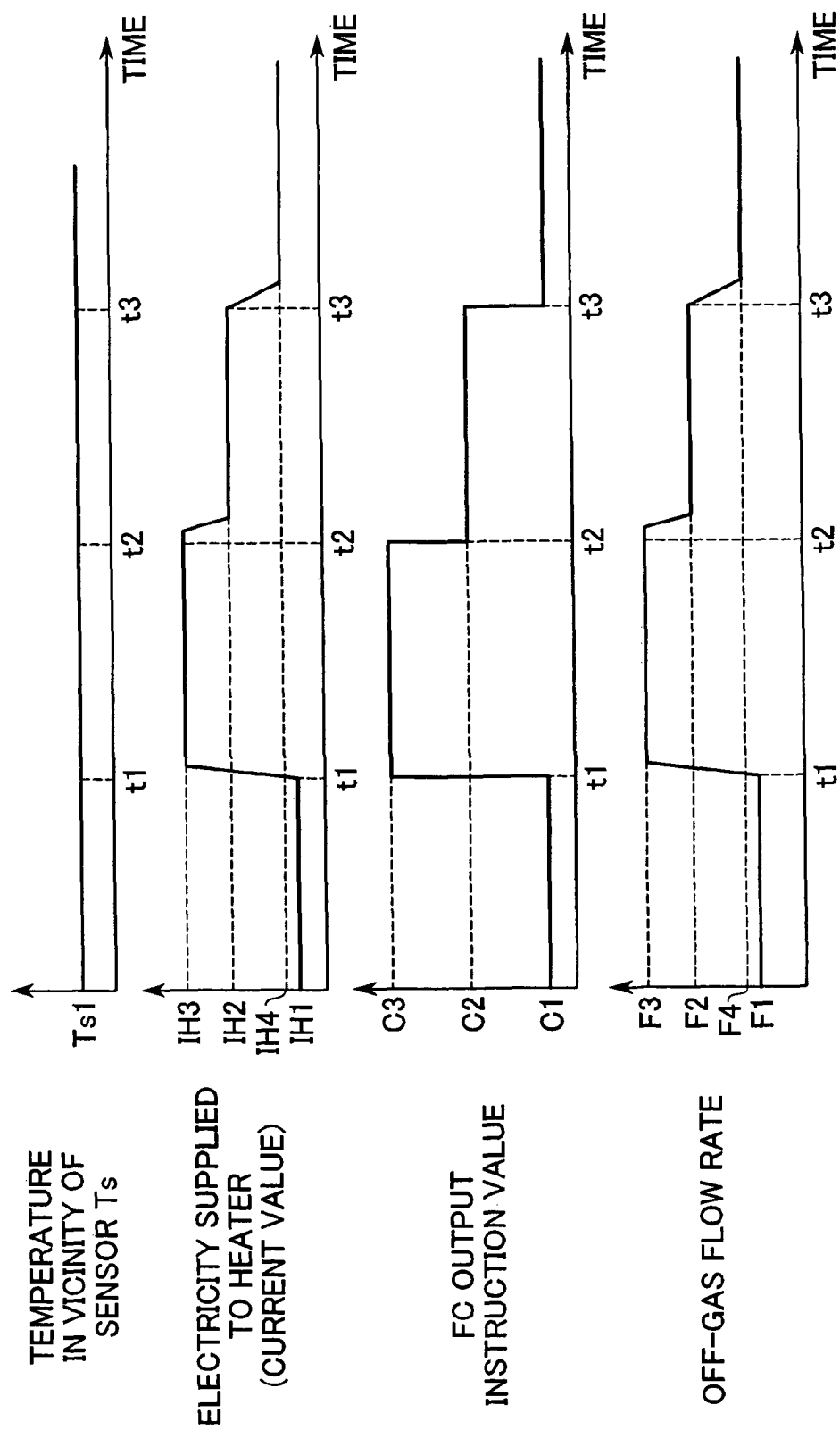
FIG. 6 is a timing chart for during operation of a fuel cell, showing an example of changes over time in the temperature in the vicinity of the gas sensor, the state of supply of electricity to the heater, the electricity generation instruction for the fuel cell, and the amount of off-gas flowing through the outlet pipe.
Figure 7:
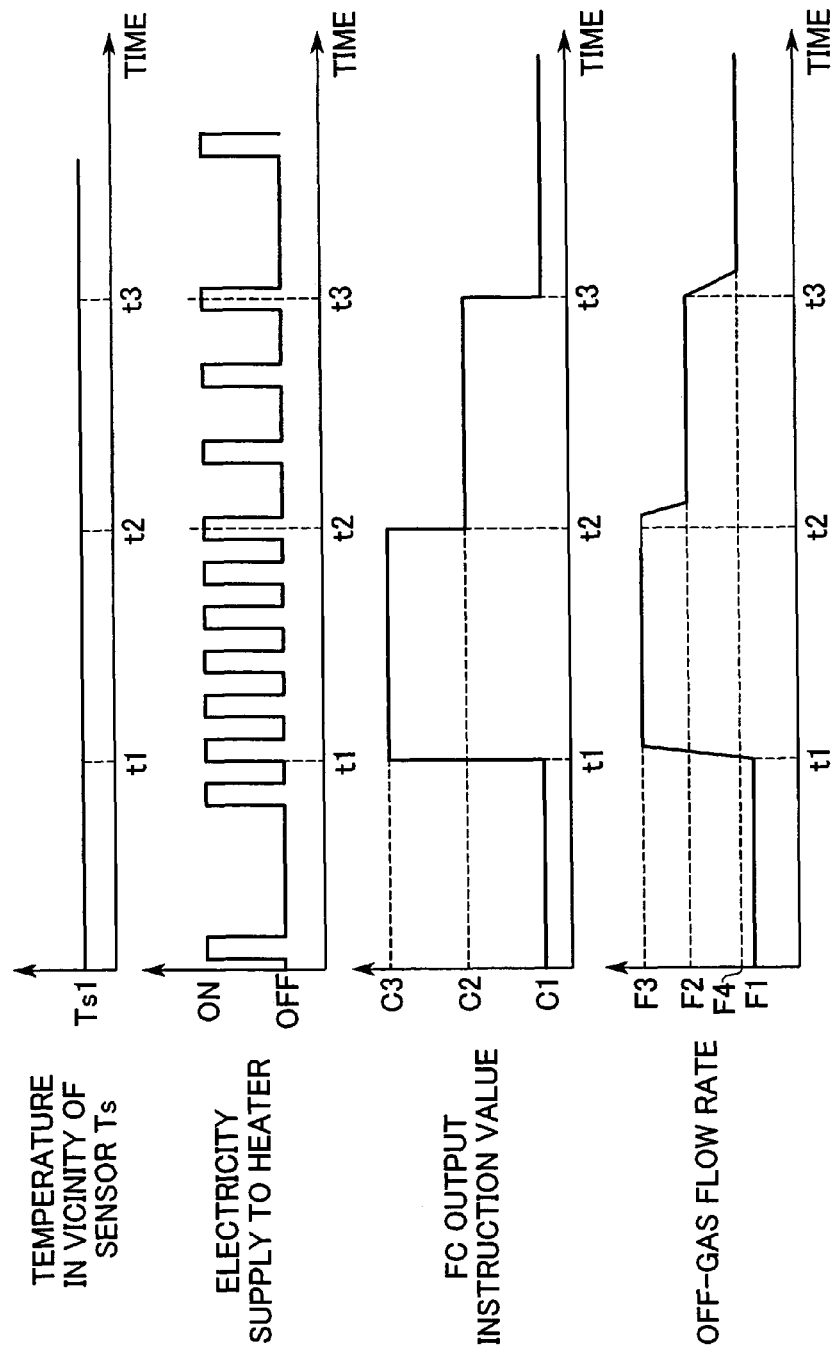
FIG. 7 is a timing chart for during operation of the fuel cell, showing an example of changes over time in the temperature in the vicinity of the gas sensor, the state of supply of electricity to the heater, the electricity generation instruction for the fuel cell, and the amount of off-gas flowing through the outlet pipe.
Figure 8:
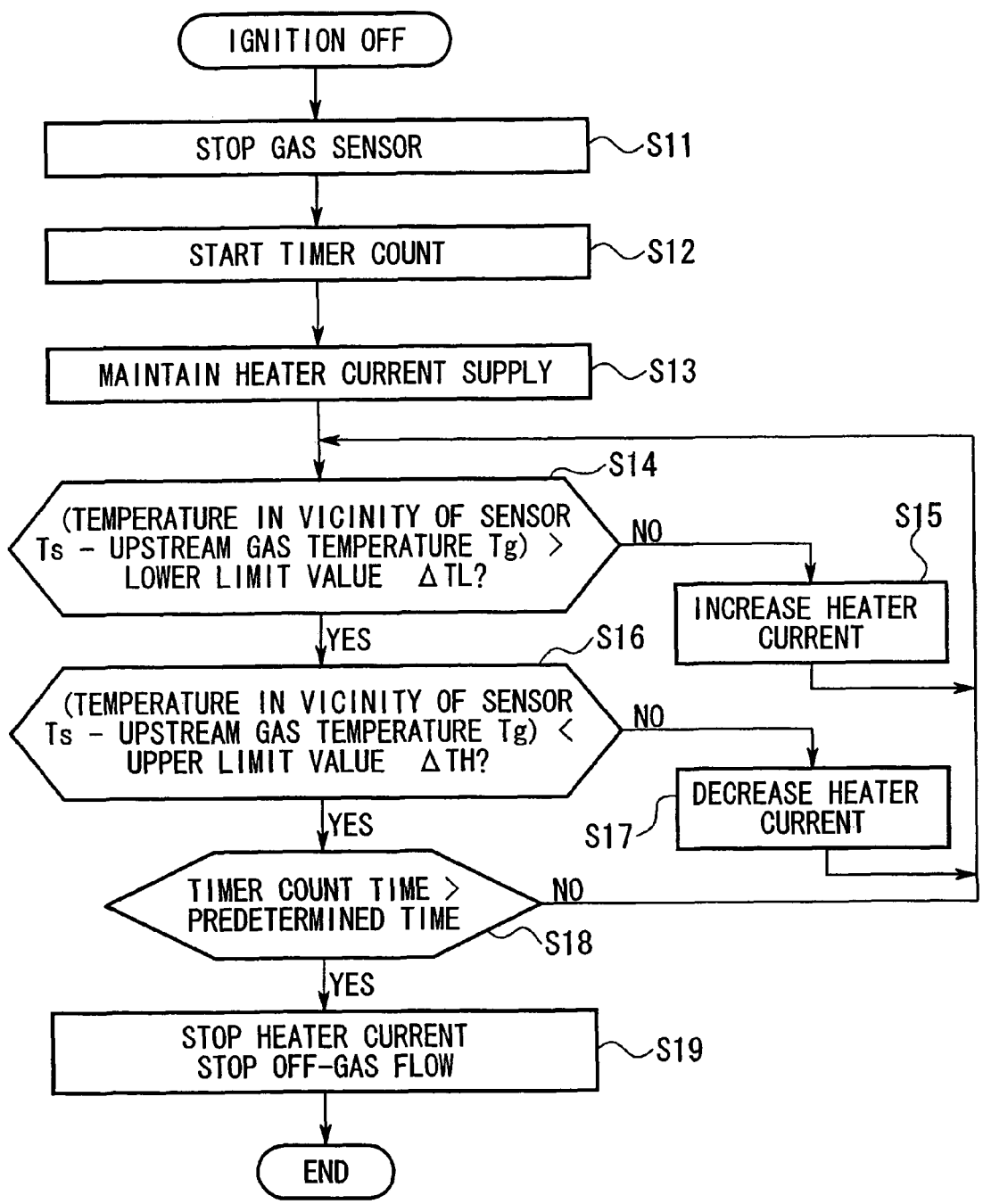
FIG. 8 is a flowchart showing a method of stopping a gas sensor with a built-in heater when the automobile ignition switch is turned OFF.
Figure 9:
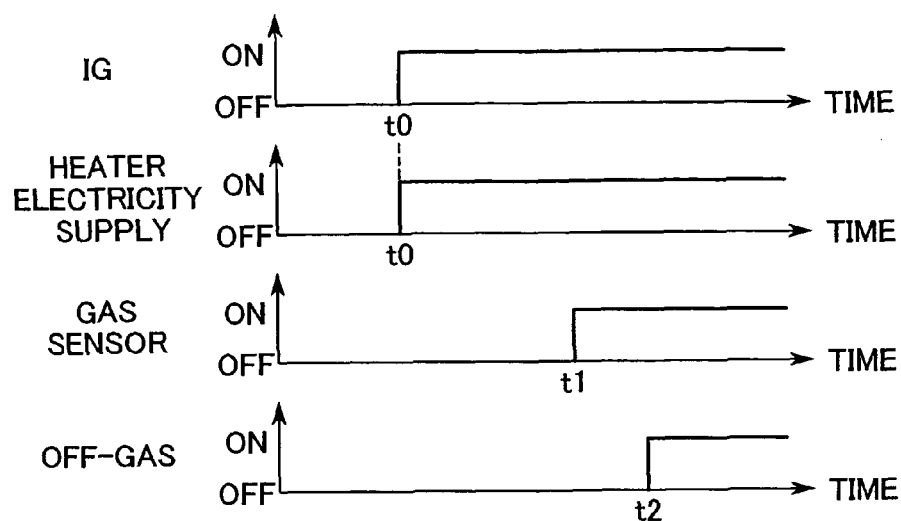
Figure 10:
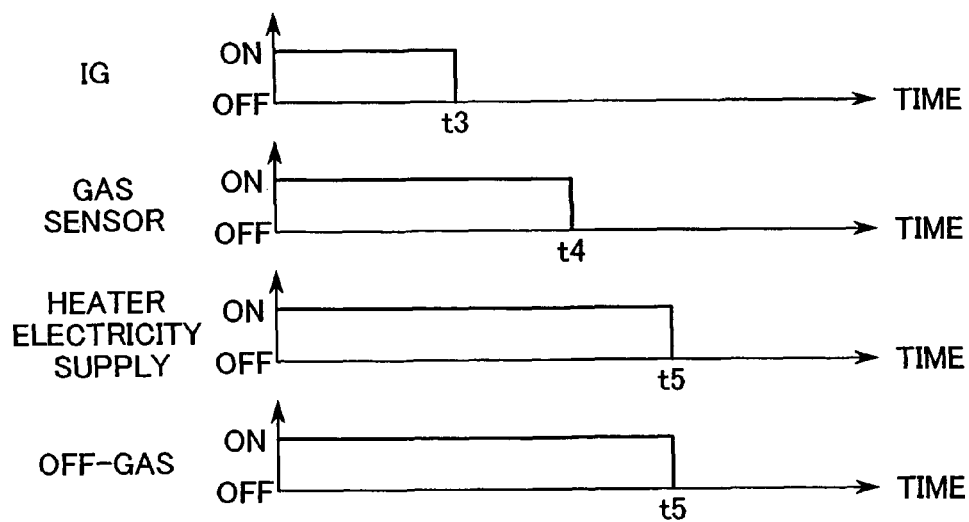
FIG. 10 is a timing chart showing the state of the heater and gas sensor, and the state of flow of off-gas, when the automobile ignition switch is turned OFF.

FIG. 5 is a flowchart showing the method of starting a gas sensor with a built-in heater when an automobile ignition switch is turned ON, FIG. 6 and FIG. 7 are timing charts showing an example of changes over time in the temperature in the vicinity of the gas sensor 15, the state of supply of electricity to the heater 27, the electricity generation instruction for the fuel cell 2, and the amount of off-gas flowing through the outlet pipe 14, during operation of the fuel cell. FIG. 8 is a flowchart showing the method of stopping the gas sensor with a built-in heater when the automobile ignition switch is turned OFF. FIG. 9 is a timing chart showing the state of the heater 27 and the gas sensor 15, and the state of flow of off-gas, when the automobile ignition switch is turned ON. FIG. 10 is a timing chart showing the state of the heater 27 and the gas sensor 15, and the state of flow of off-gas, when the automobile ignition switch is turned OFF.

Hereunder is a description of the method of starting the gas sensor 15.

Firstly, when the automobile ignition switch is turned ON, then in step S01 shown in FIG. 5, a predetermined initial setting heater current is supplied to the heater 27. The flow then proceeds to step S02 and the appropriate timer count is started.

In step S03, it is determined whether the temperature in the vicinity of the gas sensor 15 (gas temperature of gas detection chamber 24) Ts detected by the temperature sensor 28 is greater than a predetermined start temperature #Ti (for example, 100° C.) or not.

When the determination is "YES", the flow proceeds to step S05 described below.

On the other hand, when the determination is "NO", the flow proceeds to step S04.

In step S04, it is determined whether the timer count time is greater than a predetermined electricity supply time (for example 10 seconds) or not.

When the determination is "NO", the flow returns to step S03 mentioned above.

On the other hand, when the determination is "YES", the flow proceeds to step S05.

In step S05, the gas sensor 15 is started.

Then in step S06, the flow of off-gas is started in the outlet pipes 13 and 14, that is to say, the reactant gas including the oxidant or hydrogen is supplied to the fuel cell 2 so that generation of electricity by the fuel cell 2 starts, and the series of processing is complete.

For example, as shown in FIG. 9, when the ignition switch is turned ON at time t0, the predetermined initial setting heater current is supplied to the heater 27.

Then when the temperature in the vicinity of the gas sensor 15 (gas temperature of gas detection chamber 24) Ts becomes greater than the predetermined start temperature #Ti (for example, 100° C.), or when the time t1 at which the predetermined electricity supply time after the start of supply of electricity to the heater 27 has elapsed, the gas sensor 15 is started.

The flow of off-gas is started simultaneously with starting of the gas sensor 15, or at time t2 after starting.

As a result, the gas sensor 15 can be started in a state wherein the occurrence of condensation has been reliably prevented.

Hereunder is a description of the method of operating the gas sensor 15.

For example, as shown in FIG. 6, the value of the current supplied to the heater 27 is set for example by feedback control in accordance with the electricity generation instruction for the fuel cell 2 (FC output instruction value), or for example, the detected value of the amount of off-gas flowing through the outlet pipe 14 related to the amount of air supplied to the fuel cell 2 from the air compressor 7, so that the temperature in the vicinity of the gas sensor 15 (gas temperature of gas detection chamber 24) Ts becomes a predetermined temperature.

For example, at the time t1 shown in FIG. 6, when the flow rate of off-gas changes in an increasing trend from the flow rate F1 to the flow rate F3 (F1<F3), accompanying the change of the FC output instruction value from the instruction value C1 to the instruction value C3 (C1<C3), the value of the current supplied to the heater 27 is increased from the current value IH1 to the current value IH3 (IH1<IH3).

Moreover, for example, at the time t2 shown in FIG. 6, when the flow rate of off-gas changes in a decreasing trend from the flow rate F3 to the flow rate F2 (F1>F2), accompanying the change of the FC output instruction value from the instruction value C3 to the instruction value C2 (C3>C2), the value of the current supplied to the heater 27 is decreased from the current value IH3 to the current value IH2 (IH3>IH2).

Furthermore, for example, at the time t3 shown in FIG. 6, when the flow rate of off-gas changes in a decreasing trend from the flow rate F2 to the flow rate F4 (F2>F4), accompanying the change of the FC output instruction value from the instruction value C2 to the instruction value C1 (C2>C1), the value of the current supplied to the heater 27 is decreased from the current value IH2 to the current value IH4 (IH2>IH4).

As a result, the temperature Ts in the vicinity of the gas sensor 15 is set to maintain the predetermined temperature TS1 irrespective of the load state of the fuel cell 2.

Chopper control (that is to say, electricity on/off switching control) can also be employed for control of the amount of electricity supplied to the heater 27 as shown, for example, in FIG. 7, and for example, at the time t1 shown in FIG. 7, when the flow rate of off-gas changes in an increasing trend from the flow rate F1 to the flow rate F3 (F1<F3), accompanying the change of the FC output instruction value from the instruction value C1 to the instruction value C3 (C1<C3), the duty for the electricity supplied to the heater 27, that is to say, the on/off ratio, is increased.

For example, at the time t2 shown in FIG. 7, when the flow rate of off-gas changes in a decreasing trend from the flow rate F3 to the flow rate F2 (F1>F2), accompanying the change of the FC output instruction value from the instruction value C3 to the instruction value C2 (C3>C2), the duty for the electricity supplied to the heater 27 is decreased.

Furthermore, for example, at the time t3 shown in FIG. 7, when the flow rate of off-gas changes in a decreasing trend from the flow rate F2 to the flow rate F4 (F2>F4), accompanying the change of the FC output instruction value from the instruction value C2 to the instruction value C1 (C2>C1), the duty for the electricity supplied to the heater 27 is further decreased.

Hereunder is a description of the method of stopping the gas sensor 15.

Firstly, when the automobile ignition switch is turned OFF, generation of electricity by the fuel cell 2 is stopped. In step S11 shown in FIG. 8, the supply of electric power to the gas sensor 15 is stopped, the flow proceeds to step S12, and the appropriate timer count is started. Electricity is supplied to the heater 27 at this stage.

Then in step S13, supply of electricity to the heater 27 is maintained, and the flow proceeds to step S14.

In step S14 it is determined whether the temperature difference $\Delta T$ between the temperature in the vicinity of the gas sensor 15 (gas temperature of gas detection chamber 24) Ts detected by the temperature sensor 28, and the upstream gas temperature Tg detected by the temperature sensor 35 upstream of the gas sensor 15 is greater than a predetermined lower limit value $\Delta TL$ or not.

When the determination is "NO", the flow proceeds to step S15, the current supplied to the heater 27 is increased, and the flow returns to step S14. As a result, the gas temperature Ts inside the gas detection chamber 24 is increased, and the temperature difference $\Delta T$ with the upstream gas temperature Tg upstream of the gas sensor 15 is secured, and a fixed temperature difference is ensured, to reliably prevent the occurrence of condensation on the gas sensor 15.

On the other hand, when the determination is "YES", the flow proceeds to step S16.

In step S16, it is determined whether the temperature difference $\Delta T$ between the temperature in the vicinity of the gas sensor 15 (gas temperature of gas detection chamber 24) Ts detected by the temperature sensor 28, and the upstream gas temperature Tg is less than the predetermined upper limit value $\Delta TH$ or not.

When the determination is "NO", the flow proceeds to step S17, the current supplied to the heater 27 is decreased, and the flow returns to step S14. As a result, the gas temperature Ts inside the gas detection chamber 24 is decreased, and the temperature difference $\Delta T$ with the upstream gas temperature Tg upstream is reduced to ensure that electric power is not wasted.

On the other hand, when the determination is "YES", the flow proceeds to step S18.

In step S18 it is determined whether the timer count time is greater than the predetermined time or not.

When the determination is "NO", the flow returns to step S13.

On the other hand, when the determination is "YES", the flow proceeds to step S19, the supply of electricity to the heater 27 is stopped, the flow of off-gas is stopped, and the series of processing is complete.

That is to say, in the aforementioned step S14 and step S16, the temperature difference ΔT between the gas temperature Ts inside the gas detection chamber 24 of the gas sensor 15, and the upstream gas temperature Tg is maintained within a predetermined range between the upper limit value ΔTH and the lower limit value ΔTL. The gas temperature Ts in the vicinity of the gas sensor 15 is made greater than the upstream gas temperature Tg, and the temperature difference ΔT within the predetermined range (upper limit value ΔTH>ΔT> lower limit value ΔTL) is ensured therebetween.

That is to say, for example as shown in FIG. 10, at an appropriate time t4 after the ignition switch is turned OFF at time t3, the supply of electric power to the gas sensor 15 is stopped.

Moreover, the temperature difference ΔT between the gas temperature Ts inside the gas detection chamber 24 and the upstream gas temperature Tg is maintained within the predetermined range between the upper limit value ΔTH and the lower limit value ΔTL, and the supply of electricity to the heater 27 is stopped at the time t5 after the predetermined time has elapsed after operation of the gas sensor 15 is stopped.

As a result, the gas sensor 15 can be stopped in a state wherein the occurrence of condensation has been reliably prevented.

Furthermore, the flow of off-gas is continued until the time t5 at which the supply of electricity to the heater 27 is stopped, so that moisture remaining within the fuel cell 2 and the outlet pipe 14 is discharged. As a result, the gas sensor 15 can be stopped in a state wherein the occurrence of condensation has been further reliably prevented.

As described above, according to the control apparatus 1 of the gas sensor with a built-in heater according to the present embodiment, the off-gas at the oxygen electrode discharged from the fuel cell 2 and flowing through the outlet pipe 14, and which reaches the gas detection chamber 24 of the gas sensor 15 has a temperature difference within the predetermined range greater than the upstream gas and is heated by the heater 27. Therefore it is in a state wherein relative humidity is decreased in comparison to the upstream gas.

As a result, a state occurs inside the gas sensor wherein the temperature difference has a margin with respect to the duepoint temperature, and condensation of the moisture in the off-gas inside the gas sensor 15 can be reliably prevented. Therefore contact of the condensation with the detection element 29 inside the gas sensor 15, and damage to and deterioration of the detection element 29, can be prevented, durability of the detection element 29 can be improved, and accuracy of detection can be improved.

Here, regarding the gas inside the gas detection chamber 24 which is heated to a higher temperature than the upstream gas temperature Tg by the heater 27, the controller 10 sets the temperature difference ΔT with the upstream gas temperature Tg to within the predetermined range between the upper limit value ΔTH and the lower limit value ΔTL. Therefore there is no longer the problem of the temperature difference ΔT being too small (ΔT≦ΔTL) so that condensation occurs on the gas sensor 15, or the temperature difference ΔT being greater than necessary (ΔT≧ΔTH) so that electric power is wasted, and the occurrence of condensation on the gas sensor 15 can be reliably prevented with minimum energy.

Furthermore, the heater 27 is operated prior to starting the gas sensor 15 so that the gas sensor 15 can be started in a state wherein the occurrence of condensation is reliably prevented. Moreover, by starting the flow of off-gas at the time of, or after, starting the gas sensor 15, missed detection and the like of the off-gas can be reliably prevented, while preventing the occurrence of condensation on the gas sensor 15, in particular due to highly humid fuel cell 2 off-gas.

Furthermore, the supply of electricity to the heater 27 is maintained when the gas sensor 15 is stopped, and the heater 27 can be stopped in a state wherein the occurrence of condensation is reliably prevented, in preparation for, for example, restarting the gas sensor 15.

Moreover, during operation of the fuel cell 2, by controlling the amount of electricity supplied to the heater 27 in accordance with the load state and operation state of the fuel cell 2, the temperature state inside the gas detection chamber 24 can be maintained in a desired state, even if the load state and operation state of the fuel cell 2 changes.

The present invention is not limited to the aforementioned embodiments. For example, the position and the shape of the heater 27 provided in the gas detection chamber 24 of the gas sensor 15 are not limited to the embodiments.

In the present embodiment, as in the processing in step S03 through step S05 shown in FIG. 5, even if the temperature Ts in the vicinity of the gas sensor 15 detected by the temperature sensor 28 is equal to or less than the predetermined temperature #Ti at start, the gas sensor 15 was started if the timer count time exceeded the predetermined electricity supply time. However, the processing is not limited to this, and for example, step S04 may be omitted, and when the determination in step S03 is "NO", the flow may be repeated until the result is "YES".

Furthermore, in the present embodiment, for example, step S02 through step S04 may be omitted, and start of supply of electricity to the heater 27, and starting of the gas sensor 15, that is to say, start of supply of electricity to the detection element 29 and the temperature compensation element 30 may be executed simultaneously.

In the aforementioned embodiment, for example, as shown in step S11 through step S19, after supply of electric power to the gas sensor 15 was stopped the supply of electricity to the heater 27 and the flow of off-gas inside the outlet pipe 14 were stopped. However, the processing is not limited to this, and the flow of off-gas inside the outlet pipe 14 may be stopped prior to stopping the supply of electric power to the gas sensor 15 (that is to say, supply of electricity to the detection element 29 and the temperature compensation element 30).

Figure 11:
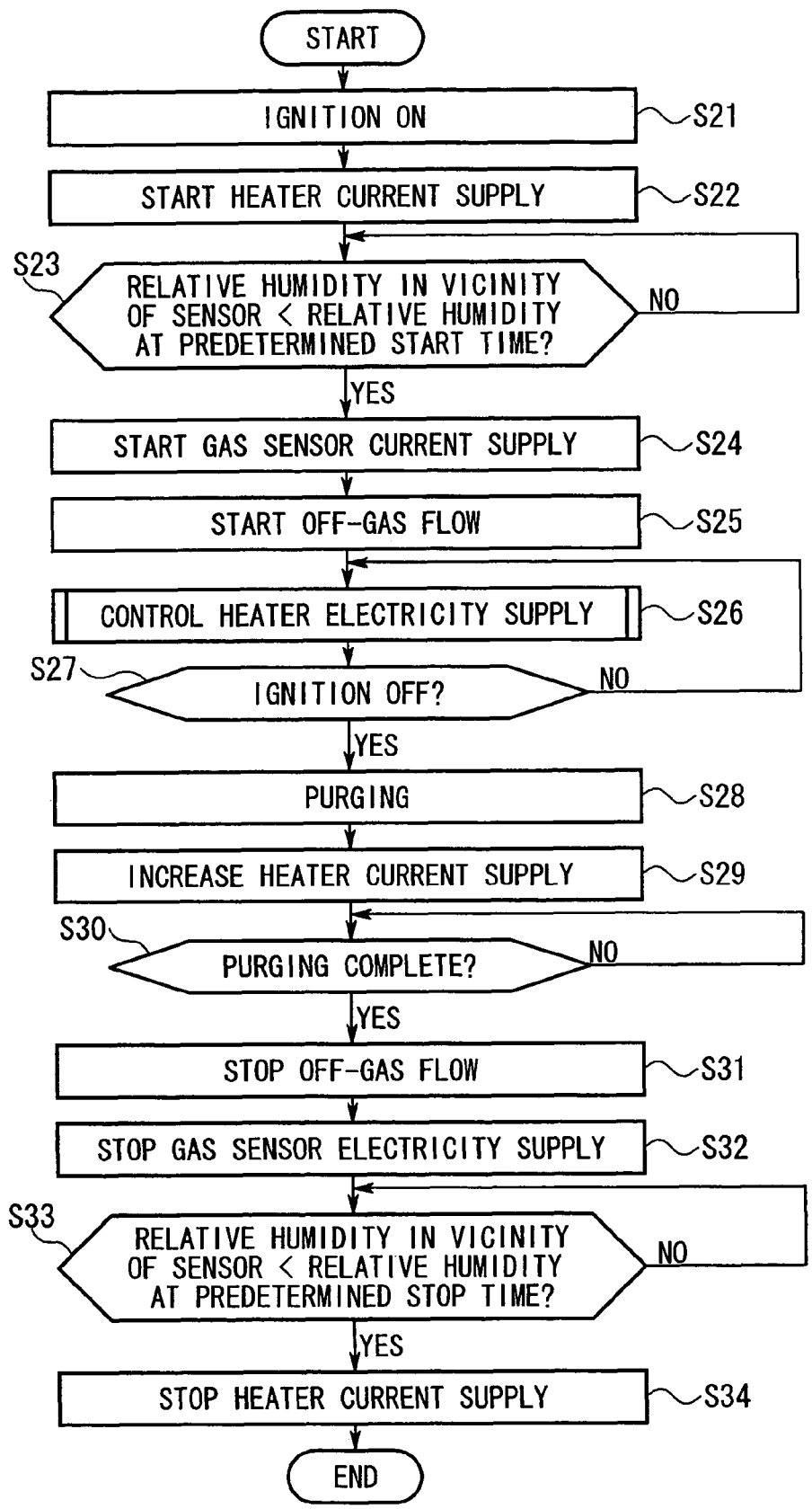
FIG. 11 is a flowchart showing the methods of starting, operating, and stopping a gas sensor with a built-in heater according to a modified example of the present embodiment.

For example, in the flowchart showing the methods of starting, operating, and stopping the gas sensor with a built-in heater according to a modified example of the present embodiment shown in FIG. 11, at first in step S21 the automobile ignition switch is turned ON, and then in step S22 the predetermined initial setup heater current is supplied to the heater 27.

Figure 12:
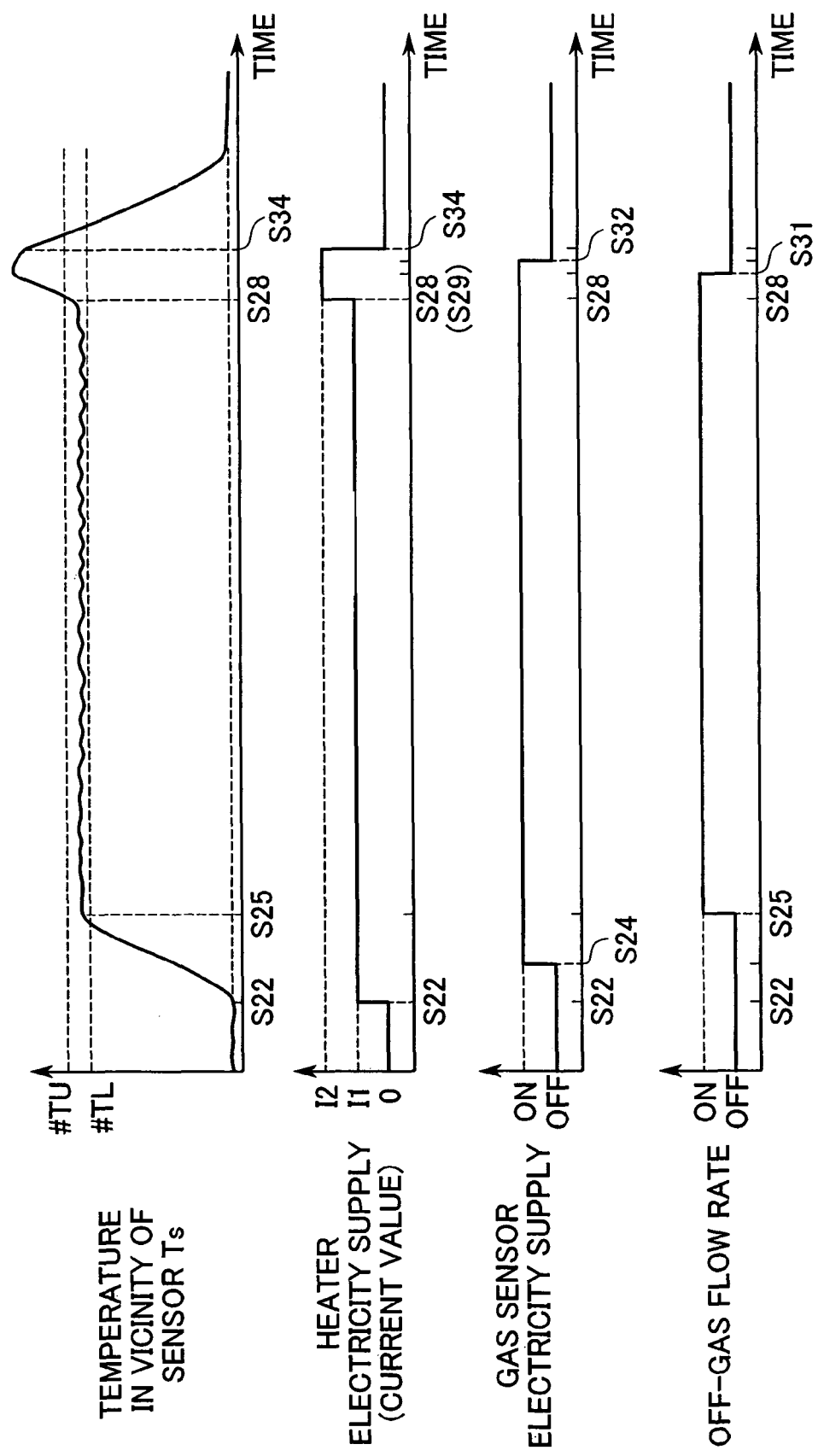
FIG. 12 is a timing chart showing an example of changes over time in the temperature in the vicinity of the gas sensor, the state of supply of electricity to the heater, the state of supply of electricity to the gas sensor, and the amount of off-gas flowing in the outlet pipe, according to a modified example of the present embodiment.

As a result, for example as shown in FIG. 12, supply of the current value I1 to the heater 27 is started, and the temperature in the vicinity of the gas sensor 15 (gas temperature of gas detection chamber 24) Ts changes in an increasing trend.

Next, in step S23, it is determined whether the relative humidity in the vicinity of the gas sensor 15 is less than the predetermined relative humidity at start #Hi or not.

When the determination is "YES", the flow proceeds to step S24.

On the other hand, when the determination is "NO", the flow returns to step S23.

In step S24, supply of electricity to the gas sensor 15, that is to say, supply of electricity to the detection element 29 and the temperature compensation element 30, begins.

Next, in step S25, for example, when the predetermined electricity supply time after the start of supply of electricity to the heater 27 has elapsed or later, and for example, as shown in FIG. 12, when the temperature in the vicinity of the gas sensor 15 (gas temperature of gas detection chamber 24) Ts becomes greater than the predetermined lower limit temperature #TL (for example, 100° C.) or later, the flow of off-gas in the outlet pipe 14 is started.

In step S26, feedback control is performed on the value of the current supplied to the heater 27, in accordance with, for example, the electricity generation instruction for the fuel cell 2 (FC output instruction value), or for example, the detected value of the amount of off-gas flowing through the outlet pipe 14 related to the amount of air supplied to the fuel cell 2 from the air compressor 7, to thereby control the temperature in the vicinity of the gas sensor 15 (gas temperature of gas detection chamber 24) Ts so that for example it becomes a set temperature greater than a predetermined lower limit temperature #TL (for example, 100° C.), or less than a predetermined upper limit temperature #TU (for example, 110° C.).

Then in step S27, it is determined whether the automobile ignition switch is turned OFF or not.

When the determination is "NO", the flow returns to step S26.

On the other hand, when the determination is "YES", the flow proceeds to step S28.

In step S28, for example, the amount of off-gas flowing inside the outlet pipes 13 and 14 is increased, and purging to discharge water remaining in the fuel cell system 1a and the like, to the outside is commenced.

Then in step S29, the amount of electricity supplied to the heater 27 is increased synchronized with the start of purging, for example, simultaneously.

As a result, for example, as shown in FIG. 12, the current value of the current supplied to the heater 27 is increased from the current value I1 to the current value I2, and the temperature in the vicinity of the gas sensor 15 (gas temperature of gas detection chamber 24) Ts rises to exceed the predetermined upper limit temperature #TU.

Then in step S30, it is determined whether purging is complete or not.

When the determination is "NO", the flow returns to step S30.

On the other hand, when the determination is "YES", the flow proceeds to step S31.

In step S31, the off-gas flowing inside the outlet pipes 13 and 14 is stopped.

Next, in step S32, the supply of electricity to the gas sensor 15, that is to say, the supply of electricity to the detection element 29 and the temperature compensation element 30 is stopped.

Next, in step S33, it is determined whether the relative humidity in the vicinity of the gas sensor 15 is less than a predetermined stopped relative humidity #Hs or not.

When the determination is "YES", the flow proceeds to step S34.

On the other hand, when the determination is "NO", the flow returns to step S33.

Then in step S34, the supply of electricity to the heater 27 is stopped, and the series of processing is complete.

According to the aforementioned modified example, the supply of electricity to the detection element 29 and the temperature compensation element 30 can be started after the relative humidity inside the gas detection chamber 24 has been reliably decreased. Therefore supply of electricity to the elements 29 and 30 in a state wherein condensation occurs on the catalyst of the detection element 29, can be prevented, and the gas sensor 15 can be started in a state wherein the occurrence of condensation on the elements 29 and 30 can be reliably prevented.

Moreover, since the heater 27 is in the continuous operation state while the fuel cell 2 is in the operation state, the occurrence of condensation on the gas sensor 15 can be reliably prevented, and missed detection and the like of the hydrogen gas can be suppressed.

Furthermore, even in the case where the flow rate of off-gas is changed in accordance with the load state of the fuel cell 2 related to the electricity generation instruction for the fuel cell 2, and the humidity state inside the gas detection chamber 24 changes due to the amount of moisture in the off-gas varying with the change in this flow rate of off-gas, that is to say, the load state of the fuel cell 2, the occurrence of condensation inside the gas detection chamber 24 can be prevented by maintaining the humidity state inside the gas detection chamber 24 in a predetermined state.

Moreover, since supply of electricity to the detection element 29 and the temperature compensation element 30 is stopped after the flow of off-gas is stopped, the occurrence of missed detection and the like with respect to the hydrogen-gas can be suppressed, while preventing condensation on the gas sensor 15, in particular due to highly humid off-gas of the fuel cell 2. Furthermore, since the relative humidity inside the gas detection chamber 24 can be decreased beforehand, a state wherein condensation occurs on the gas sensor 15 at the time of the next start can be prevented.

Moreover, when the fuel cell 2 is stopped, then even when purging is executed, by temporarily increasing the temperature inside the gas detection chamber 24, it is possible to prevent an increase in the amount of saturated water vapor and the occurrence of condensation inside the gas detection chamber 24, and the time for which the electricity is supplied continuously to the heater while operation is stopped can be decreased.

In the aforementioned modified example, the amount of electricity supplied to the heater 27 is increased simultaneously with the start of executing purging. However, the processing is not limited to this, and for example, the amount of electricity supplied to the heater 27 may be increased for example at the point when the start of purging is permitted, that is to say, prior to the start of purging.

Moreover, in the aforementioned modified example, when the gas sensor 15 is stopped, the amount of electricity supplied to the heater 27 may be temporarily increased irrespective of whether purging is employed or not. Furthermore, the amount of electricity supplied to the heater 27 may be temporarily increased after stopping the flow of off-gas.

That is to say, by temporarily increasing the amount of electricity supplied to the heater 27 when the gas sensor 15 is stopped, the time required to decrease the relative humidity in the vicinity of the gas sensor 15 to less than the predetermined stopped relative humidity #Hs can be shortened, and the time required until the supply of electricity to the heater 27 is stopped, that is to say, the time required for the series of stopping operations can be shortened.

In the aforementioned modified example, for example, when the gas sensor with a built-in heater 15 is started, step S23 may be omitted, and the start of supply of electricity to the heater 27 may be synchronized with starting of the gas sensor 15, that is to say, the start of supply of electricity to the detection element 29 and the temperature compensation element 30, and for example, executed simultaneously.

In this case, the gas sensor with a built-in heater 15 can be started in a state wherein the occurrence of condensation on the detection element 29 and the temperature compensation element 30 is prevented, while preventing an increase in electric power consumption due to starting supply of electricity to the heater 27 too early, for example under a low-humidity environment. Furthermore, control when starting the heater 27 and the gas sensor 15 can be simplified.

Furthermore, for example, when the gas sensor with a built-in heater 15 is stopped, step S33 may be omitted, and stopping the gas sensor 15, that is to say, stopping supply of electricity to the detection element 29 and the temperature compensation element 30 may be synchronized with stopping supply of electricity to the heater 27, and for example, executed simultaneously.

In this case, the heater 27 can be stopped in a state wherein the occurrence of condensation on the detection element 29 and the temperature compensation element 30 is prevented, while preventing an increase in electric power consumption due to stopping the supply of electricity to the heater 27 too late, for example under a low-humidity environment. Furthermore, control when stopping the heater 27 and the gas sensor 15 can be simplified.

Moreover, in the aforementioned modified example, for example, when the gas sensor with a built-in heater 15 is stopped, step S33 may be omitted, and the supply of electricity for the heater 27 may be continued for a predetermined time after stopping the gas sensor 15, that is to say, after stopping the supply of electricity to the detection element 29 and the temperature compensation element 30, and the supply of electricity to the heater 27 may be stopped after this predetermined time has elapsed.

In this case, the gas sensor 15 can be stopped in a state wherein the occurrence of condensation on the detection element 29 and the temperature compensation element 30 inside the gas detection chamber 24 has been prevented. Furthermore, since the relative humidity inside the gas detection chamber 24 can be decreased in advance ready for at the time of the next start, a state wherein condensation occurs on the gas sensor 15 at the time of the next start can be prevented, and the time required for starting can be shortened.

In the aforementioned embodiment, the gas sensor 15 was arranged in the outlet pipe 14 on the oxygen electrode side of the fuel cell 2. However it is not limited to this configuration, and may be arranged in another position, in particular, in a position such as where the relative humidity of the atmosphere gas is relatively high. In this case, damage to, deterioration of, and reduction in detection accuracy of, the gas sensor can be prevented, and accurate detection performed.

As described above, according to the method of starting a gas sensor with a built-in heater in the first embodiment of the present invention, by starting operation of the heater prior to starting operation of the gas sensor with a built-in heater, the gas sensor with a built-in heater can be started in a state wherein the occurrence of condensation has been prevented.

Moreover, according to the method of starting a gas sensor with a built-in heater in the second embodiment of the present invention, by setting the temperature inside the gas detection chamber higher than the predetermined threshold temperature, the gas sensor with a built-in heater can be started in a state wherein the occurrence of condensation has been reliably prevented.

Furthermore, according to the method of starting a gas sensor with a built-in heater in the third embodiment of the present invention, by starting the flow of cathode off-gas of the fuel cell to the flow tube at or after operation of the gas sensor with a built-in heater, the occurrence of missed detection and the like with respect to the hydrogen gas within the cathode off-gas can be reliably prevented.

Moreover, according to the method of starting a gas sensor with a built-in heater in the fourth or fifth embodiment of the present invention, the occurrence of missed detection and the like with respect to the hydrogen gas flowing through the off-gas piping can be suppressed while preventing condensation on the gas sensor with a built-in heater, particularly due to off-gas from a high-humidity fuel cell.

Furthermore, according to the method of starting a gas sensor with a built-in heater in the sixth embodiment of the present invention, the gas sensor with a built-in heater can be started in a state wherein the occurrence of condensation on the detection element and the temperature compensation element is prevented, while preventing an increase in electric power consumption due to starting supply of electricity to the heater too early. Furthermore, control when starting the heater and the gas sensor with a built-in heater can be simplified.

Moreover, according to the method of starting a gas sensor with a built-in heater in the seventh embodiment of the present invention, the gas sensor with a built-in heater can be started in a state wherein the occurrence of condensation on the detection element and the temperature compensation element is reliably prevented.

Furthermore, according to the method of starting a gas sensor with a built-in heater in the eighth embodiment of the present invention, the supply of electricity to the detection element and the temperature compensation element can be started after reliably reducing the relative humidity inside the gas detection chamber. Therefore supply of electricity to each element in a state where condensation has occurred on the catalyst and the like of the detection element can be prevented, and the gas sensor with a built-in heater can be started in a state wherein the occurrence of condensation on the elements has been reliably prevented.

Moreover, according to the method of stopping a gas sensor with a built-in heater in the ninth embodiment of the present invention, by stopping operation of the gas sensor with a built-in heater prior to stopping operation of the heater, then for example, in preparation for restart or the like of the gas sensor with a built-in heater, the heater can be stopped in a state wherein the occurrence of condensation has been prevented.

Furthermore, according to the method of stopping a gas sensor with a built-in heater in the tenth embodiment of the present invention, by setting the temperature inside the gas detection chamber to a value of a predetermined temperature range which is higher than the temperature of the detection gas, the heater can be stopped in a state wherein the occurrence of condensation is reliably prevented.

Moreover, according to the method of stopping a gas sensor with a built-in heater in the eleventh embodiment of the present invention, moisture within the flow tube can be removed by the flow of off-gas, and the occurrence of condensation on the gas sensor with a built-in heater while stopped, can be better prevented.

Furthermore, according to the method of stopping a gas sensor with a built-in heater in the twelfth or the thirteenth embodiments of the present invention, the occurrence of missed detection and the like with respect to the hydrogen gas flowing through the off-gas piping can be suppressed while preventing condensation on the gas sensor with a built-in heater, particularly due to off-gas from a high-humidity fuel cell. Moreover, since the relative humidity inside the gas detection chamber can be decreased beforehand in preparation for the next start, a state wherein condensation occurs on the gas sensor with a built-in heater at the time of the next start can be prevented.

Furthermore, according to the method of stopping a gas sensor with a built-in heater in the fourteenth embodiment of the present invention, the heater can be stopped in a state wherein the occurrence of condensation on the detection element and the temperature compensation element has been prevented for example in preparation for the next start of the gas sensor with a built-in heater, while preventing an increase in power consumption due to stopping supply of electricity to the heater too late, for example, under a low-humidity environment. Moreover, control when stopping the heater and the gas sensor with a built-in heater can be simplified.

Furthermore, according to the method of stopping a gas sensor with a built-in heater in the fifteenth embodiment of the present invention, the heater can be stopped in a state wherein the occurrence of condensation on the detection element and the temperature compensation element is reliably prevented.

Moreover, according to the method of stopping a gas sensor with a built-in heater in the sixteenth embodiment of the present invention, the gas sensor with a built-in heater can be stopped in a state wherein the occurrence of condensation on the detection element and the temperature compensation element has been prevented. Furthermore, since the relative humidity inside the gas detection chamber can be decreased in advance ready for at the time of the next start, a state wherein condensation occurs on the gas sensor with a built-in heater at the time of the next start can be prevented, and the time required for starting can be shortened.

Moreover, according to the method of operating a gas sensor with a built-in heater in the seventeenth embodiment of the present invention, the starting, stopping and continuing operation of the gas sensor with a built-in heater can be executed in a state wherein the occurrence of condensation inside the gas detection chamber has been prevented, while suppressing the occurrence of missed detection and the like with respect to the hydrogen gas flowing in the off-gas pipe.

Furthermore, since the heater is in continuous operation while the fuel cell is in operation, the occurrence of condensation on the gas sensor with a built-in heater can be reliably prevented, and the occurrence of missed detection and the like of the hydrogen gas can be suppressed.

Moreover, according to the method of operating a gas sensor with a built-in heater in the eighteenth embodiment of the present invention, the occurrence of condensation inside the gas detection chamber due to the changing temperature inside the gas detection chamber can be reliably prevented.

Furthermore, according to the method of operating a gas sensor with a built-in heater in the nineteenth embodiment of the present invention, by temporarily increasing the temperature inside the gas detection chamber, the amount of saturated water vapor is increased, and the occurrence of condensation inside the gas detection chamber can be prevented, and the time for which the electricity is supplied continuously to the heater while operation is stopped can be shortened.

Moreover, according to the method of operating a gas sensor with a built-in heater in the twentieth embodiment of the present invention, the change in the humidity state inside the gas detection chamber due to the moisture content in the off-gas which changes due to the load state of the fuel cell, can be prevented, and the occurrence of condensation inside the gas detection chamber can be prevented, by maintaining the humidity state inside the gas detection chamber in a predetermined state.

Furthermore, according to the method of operating a gas sensor with a built-in heater in the twenty first embodiment of the present invention, the occurrence of condensation inside the gas detection chamber can be prevented by increasing the amount of electricity supplied to the heater to increase the temperature inside the gas detection chamber, particularly at the time of high load of the fuel cell when the relative humidity of the off-gas increases.

Moreover, according to the method of operating a gas sensor with a built-in heater in the twenty second embodiment of the present invention, while detecting the detection gas using the gas sensor with a built-in heater, the heater can be maintained in an operating state. Therefore, the relative humidity inside the gas detection chamber can be reliably made a low state, and the starting, stopping and continuing operation of the gas sensor with a built-in heater can be executed in a state wherein the occurrence of condensation inside the gas detection chamber has been prevented.

The invention claimed is:

1. A method of stopping a gas sensor, the method comprising:
   providing a gas sensor within a wall of a flow tube in which a detection gas having a water content flows from a fuel cell, the gas sensor including:
      a gas detection chamber into which the detection gas is introduced;
      a heater which heats an interior of the gas detection chamber; and
      a detection element which is disposed within the gas detection chamber and thermally coupled to the heater for detecting the detection gas;
   providing a controller which independently controls a supply of electricity to the heater and a supply of electricity to the detection element;
   detecting a first temperature inside the gas detection chamber;
   detecting a second temperature of the detection gas discharged from the fuel cell to the gas detection chamber at a location between the fuel cell and the gas detection chamber;
   stopping the supply of electricity to the detection element and then controlling the supply of electricity to the heater to maintain the first temperature in a predetermined temperature range, which is higher than the second temperature, for a predetermined time; and
   stopping the supply of electricity to the heater after the predetermined time has elapsed,
   wherein the step of controlling the supply of electricity to the heater comprises:
   increasing the supply of electricity to the heater when a difference between the first temperature and the second temperature is less than a lower limit value; and
   decreasing the supply of electricity to the heater when a difference between the first temperature and the second temperature is greater than an upper limit value.

2. A method of stopping a gas sensor according to claim 1, wherein the detection gas is hydrogen gas contained in the off-gas discharged from an oxygen electrode of a fuel cell, and the off-gas is flowed through the flow tube at least until after stopping the supply of electricity to the detection element.

3. A method of stopping a gas sensor according to claim 1, wherein the predetermined temperature range is determined so as to prevent condensation of the water content contained in the detection gas.

4. A method of stopping a gas sensor, the method comprising:
   providing a gas sensor within a wall of an off-gas pipe through which off-gas discharged from an oxygen electrode of a fuel cell flows, the gas sensor including:
      a gas detection chamber into which hydrogen gas contained in the off-gas is introduced as a detection gas having a water content;

a heater which is disposed within the gas detection chamber and heats an interior of the gas detection chamber;

a detection element which is furnished with a catalyst, disposed within the gas detection chamber, and thermally coupled to the heater, for detecting the detection gas; and a temperature compensation element which is disposed within the gas detection chamber, the gas sensor being a gas-contact combustion-type gas sensor which detects the concentration of the hydrogen gas in accordance with a difference in the electrical resistance value between the detection element and the temperature compensation element, produced due to heat produced by combustion when hydrogen contained in the off-gas contacts the catalyst; detecting the temperature inside the gas detection chamber and the temperature of the detection gas on an upstream side of the detection element;

providing a controller which independently controls a supply of electricity to the heater and a supply of electricity to the detection element;

stopping the flow of the off-gas; then stopping the supply of electricity to the detection element and the temperature compensation element;

detecting a first temperature inside the gas detection chamber;

detecting a second temperature of the detection gas discharged from the fuel cell to the gas detection chamber at a location between the fuel cell and the gas detection chamber;

controlling the supply of electricity to the heater to maintain the first temperature in a predetermined temperature range, which is higher than the second temperature, for a predetermined time; and then stopping the supply of electricity to the heater after the predetermined time has elapsed, wherein the step of controlling the supply of electricity to the heater comprises:

increasing the supply of electricity to the heater when a difference between the first temperature and the second temperature is less than a lower limit value; and decreasing the supply of electricity to the heater when a difference between the first temperature and the second temperature is greater than an upper limit value.

5. A method of stopping a gas sensor according to claim 4, wherein the predetermined temperature range is determined so as to prevent condensation of the water content contained in the detection gas.

6. A method of stopping a gas sensor in a fuel cell, the method comprising:

providing a gas sensor including:
- a gas detection chamber into which a detection gas having a water content is introduced;
- a detection element which is furnished with a catalyst, and disposed within the gas detection chamber;
- a temperature compensation element which is disposed within the gas detection chamber; and
- a heater capable of changing a humidity state inside the gas detection chamber;

providing a controller which independently controls a supply of electricity to the heater and a supply of electricity to the detection element;

detecting a first temperature inside the gas detection chamber;

detecting a second temperature of the detection gas discharged from the fuel cell to the gas detection chamber at a location between the fuel cell and the gas detection chamber;

stopping the supply of electricity to the detection element and the temperature compensation element;

continuing the supply of electricity to the heater for a predetermined time, after stopping the supply of electricity to the detection element and the temperature compensation element;

comparing a relative humidity inside the gas detection chamber to a predetermined relative humidity; and stopping the supply of electricity to the heater when the relative humidity inside the gas detection chamber is less than the predetermined relative humidity, to thereby decrease in advance the relative humidity inside the gas detection chamber for at the time of starting a next operation, wherein the step of controlling the supply of electricity to the heater comprises:

increasing the supply of electricity to the heater when a difference between the first temperature and the second temperature is less than a lower limit value; and decreasing the supply of electricity to the heater when a difference between the first temperature and the second temperature is greater than an upper limit value.

7. A method of operating a gas sensor, the method comprising:

providing a gas sensor within a wall of an off-gas pipe through which off-gas discharged from an oxygen electrode of a fuel cell flows, the gas sensor including:
- a gas detection chamber into which hydrogen gas contained in the off-gas is introduced as a detection gas having a water content;
- a heater which is disposed within the gas detection chamber and heats an interior of the gas detection chamber; and
- a detection element which is disposed within the gas detection chamber and thermally coupled to the heater, for detecting the detection gas, providing a controller which independently controls a supply of electricity to the heater and a supply of electricity to the detection element;

detecting a first temperature inside the gas detection chamber when starting an operation of the fuel cell;

starting the supply of electricity to the heater so as to heat the gas detection chamber, and then starting the supply of electricity to the detection element when the temperature inside the gas detection chamber exceeds a predetermined threshold temperature which is determined so as to prevent condensation of the water content contained in the detection gas;

continuing the supply of electricity to the detection element and to the heater during normal operation of the fuel cell;

detecting the first temperature inside the gas detection chamber and a second temperature of the detection gas discharged from the fuel cell to the gas detection chamber at a location between the fuel cell and the gas detection chamber;

stopping the flow of the off-gas when operation of the fuel cell is stopped; then stopping the supply of electricity to the detection element;

controlling the supply of electricity to the heater to maintain the first temperature inside the gas detection chamber in a predetermined temperature range which is higher than the second temperature of the detection gas at the location between the fuel cell and the gas detection chamber, for a predetermined time; and then stopping the supply of electricity to the heater after the predetermined time has elapsed, wherein the step of controlling the supply of electricity to the heater comprises:

increasing the supply of electricity to the heater when a difference between the first temperature and the second temperature is less than a lower limit value; and decreasing the supply of electricity to the heater when a difference between the first temperature and the second temperature is greater than an upper limit value.

8. A method of operating a gas sensor according to claim 7, comprising, during a normal operation of the fuel cell, maintaining the temperature inside the gas detection chamber of the gas sensor within a predetermined temperature range by controlling an amount of the electricity supplied to the heater.

9. A method of operating a gas sensor according to claim 8, comprising, during the normal operation of the fuel cell, increasing or decreasing the amount of electricity supplied to the heater in accordance with a load on the fuel cell.

10. A method of operating a gas sensor according to claim 8, comprising increasing the amount of electricity supplied to the heater when a load on the fuel cell increases.

11. A method of operating a gas sensor in a fuel cell, the method comprising:

providing a gas sensor including:

a gas detection chamber into which a detection gas having a water content is introduced;

a detection element which is furnished with a catalyst, and disposed within the gas detection chamber;

a temperature compensation element which is disposed within the gas detection chamber; and a heater capable of changing a humidity state inside the gas detection chamber, providing a controller which independently controls a supply of electricity to the heater and a supply of electricity to the detection element;

firstly starting the supply of electricity to the heater when starting operation of the gas sensor; and next starting the supply of electricity to the detection element and the temperature compensation element after the relative humidity inside the gas detection chamber has decreased, and then flowing the detection gas through the gas detection chamber;

continuing the supply of electricity to the heater during operation of the gas sensor; and detecting a first temperature inside the gas detection chamber;

detecting a second temperature of the detection gas discharged from the fuel cell to the gas detection chamber at a location between the fuel cell and the gas detection chamber;

firstly stopping the supply of electricity to the detection element and the temperature compensation element when stopping the operation of the gas sensor;

decreasing the relative humidity inside the gas detection chamber by continuing the supply of electricity to the heater;

comparing the relative humidity inside the gas detection chamber to a predetermined relative humidity; and next stopping the supply of electricity to the heater after the relative humidity inside the gas detection chamber is less than the predetermined relative humidity, wherein the continuing the supply of electricity to the heater comprises:

increasing the supply of electricity to the heater when a difference between the first temperature and the second temperature is less than a lower limit value; and decreasing the supply of electricity to the heater when a difference between the first temperature and the second temperature is greater than an upper limit value.

* * * * *